(12) United States Patent
Walker et al.

(10) Patent No.: US 6,403,780 B1
(45) Date of Patent: *Jun. 11, 2002

(54) **HOMOLOGOUS 28-KILODALTON IMMUNODOMINANT PROTEIN GENES OF *EHRLICHIA CANIS* AND USES THEREOF**

(75) Inventors: David H. Walker; Xue-Jie Yu; Jere W. McBride, all of Galveston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/261,358

(22) Filed: Mar. 3, 1999

Related U.S. Application Data

(63) Continuation-in-part of application No. 09/201,458, filed on Nov. 30, 1998.

(51) Int. Cl.⁷ .......................... C12N 15/00; C12N 1/20; C12N 1/14; C12N 1/16
(52) U.S. Cl. ................. 536/23.1; 536/23.5; 536/23.7; 536/24.2; 435/325; 435/252.3; 435/254.11; 435/255.1; 435/320.1; 435/326; 530/350
(58) Field of Search ............... 435/320.1, 252.3, 435/69.1, 23.1; 536/23.1

(56) References Cited

PUBLICATIONS

Ohashi et al. Cloning and Characterization of Multigenes Encoding the Immunodominant 30–kilodalton Major Outer Membrane Proteins of *Ehrlichia canis* and Application of the Recombinant Protein for Serodiagnosis. J. Clin. Microbiol. 36(9): 2671–2680, Sep. 1998.*

* cited by examiner

*Primary Examiner*—Karen Cochrane Carlson
*Assistant Examiner*—Patricia Robinson
(74) *Attorney, Agent, or Firm*—Benjamin Aaron Adler

(57) ABSTRACT

The present invention is directed to the cloning, sequencing and expression of homologous immunoreactive 28-kDa protein genes, ECa28-1 and ECa28SA3, from a polymorphic multiple gene family of *Ehrlichia canis*. A complete sequence of another 28-kDa protein gene, ECaSA2, is also provided. Further disclosed is a multigene locus encoding all five homologous 28-kDa protein genes of *Ehrlichia canis*. Recombinant *Ehrlichia canis* 28-kDa proteins react with convalescent phase antiserum from an *E. canis*-infected dog.

12 Claims, 13 Drawing Sheets

```
  1 ATTTTATTTATTACCAATCTTATATATAATATTAAATTTCTCTTACAAAAATCTCTAATG    60
 61 TTTTATACCTAATATATATATATTCTGGCTTGATCTACTTTGCACTTCCACTATTGTTAAT   120
121 TTATTTCACTATTTTAGGTGTAATATGAATTGCAAAAAATTCTTATAACAACTGCATT      180
                        M  N  C  K  K  I  L  I  T  T  A  L
181 AATATCATTAATGTACTCTATTCCAAGCATATCTTTTTCTGATACTATACAAGATGGTAA   240
     I  S  L  M  Y  S  I  P  S  I  S  F  S  D  T  I  Q  D  G  N
241 CATGGGTGGTAACTTCTATATTAGTGGGAAAGTATGTACCAAGTGTCTCACATTTTGGTAG   300
     M  G  G  N  F  Y  I  S  G  K  Y  V  P  S  V  S  H  F  G  S
301 CTTCTCAGCTAAAGAAGAAAGCAAATCAACTGTTGGAGTTTTTGGATTAAAACATGATTG   360
     F  S  A  K  E  E  S  K  S  T  V  G  V  F  G  L  K  H  D  W
361 GGATGGAAGTCCAATACTTAAGAATAAACACGCTGACTTTACTGTTCCAAACTATTCGTT   420
     D  G  S  P  I  L  K  N  K  H  A  D  F  T  V  P  N  Y  S  F
421 CAGATACGAGAACAATCCATTTCTAGGGTTTGCAGGAGCTATCGGTTACTCAATGGGTGG   480
     R  Y  E  N  N  P  F  L  G  F  A  G  A  I  G  Y  S  M  G  G
481 CCCAAGAATAGAATTCGAAATCTTATGAAGCATTCGACGTAAAAAGTCCTAATATCAA    540
     P  R  I  E  F  E  I  S  Y  E  A  F  D  V  K  S  P  N  I  N
541 TTATCAAAATGACGCGCACAGGTACTGCGCTCTATCCATCTCATCACACATCGGCAGCCATGGA   600
     Y  Q  N  D  A  H  R  Y  C  A  L  S  H  H  T  S  A  A  M  E
601 AGCTGATAAATTTGTCTTCTTAAAAAACGAAGGGTTAATTGACATATCACTTGCAATAAA   660
     A  D  K  F  V  F  L  K  N  E  G  L  I  D  I  S  L  A  I  N
661 TGCATGTTATGATATAATAATGACAAAGTACCTGTTTCCTCCTTATATATGCGCAGGTAT   720
     A  C  Y  D  I  I  N  D  K  V  P  V  S  P  Y  I  C  A  G  I
```

Fig. 1A

```
 721  TGGTACTGATTTGATTTCTATGTTTGAAGCTACAAGTCCTAAAATTCCTACCAAGGAAA  780
       G  T  D  L  I  S  M  F  E  A  T  S  P  K  I  S  Y  Q  G  K

841  CAGGATCATAGGTAATGAGTTTAGAGAGATATTCCTGCAATAGTACCTAGTAACTCAACTAC  900
       R  I  I  G  N  E  F  R  D  I  P  A  I  V  P  S  N  S  T  T

901  AATAAGTGGACCACAATTTGCAACAGTAACACTAAATGTGTCACTTTGGTTTAGAACT  960
       I  S  G  P  Q  F  A  T  V  T  L  N  V  C  H  F  G  L  E  L

961  TGGAGGAAGATTAACTTCTAATTTTATTGTTGCCACATATTAAAAATGATCTAAACTTG  1020
       G  G  R  F  N  F  (SEQ. ID NO: 2)
1021  TTTTTAWTATTGCTACATACAAAAAGAAAATAGTGGCAAAAGAATGTAGCAATAAGA  1080
1081  GGGGGGGGACCAAATTTATCTTCTATGCTTCCCAAGTTTTTCYCGCTATTTATGA  1140
1141  CTTAAACAACAGAAGTAATATATTAAATTTCTCACGGAAAACTTATCTCCAAATATTTATTTATTA  1200
1201  CCAATCTTATATATATAATATTAAATTTCTCTTACAAAATCACTAGTATTTTATACCAAAA  1260
1261  TATATATTCTGACTTGCTTTTCTTCTGCACTTCTATTTTTAATTTATTTGTCACTAT  1320
1321  TAGGTTATATAATAAWATGAATTGCMAAAGATTTTCATAGCAAGTGCATTGATATCACTAA  1380
1381  TGTCTTTCTTACCTAGCGTATCTTTTTTCTGAATCAATACATGAAGATATAAATGGTA  1440
1441  ACTTTTACATTAGTGCAAAGTATATGCCAAGTGCCTCACACTTTGGCGTATTTCAGTTA  1500
1501  AAGAAGAGAAAAACAACAACTGGAGTTTTCGGATTAAAACAAGATTGGGACGGAGCAA  1560
1561  CACTAAAGGATGCAAGCWGCAGCCACACAWTAGACCCAAGTACAATG  1607

(SEQ ID NO: 1)
```

Fig. 1B

```
EC28-1    MNCKKILITTALISLMYSIPSISFSDTIQDGNMG-GN----FYISGKYVPSVSHFGSFSAKE-----ESKSTVGVFGLKHDWDGSPILKNKHAD-FTVPNYSF  92
EC28SA2   ......VFTIS...SI.FL.NV.Y.NPVYGNS.-Y..........P...I..E.------K.K.TV.Y...EN.A.DA.SSQSPD.N..1R.....  93
EC28SA1   .KY..TFTV...VL.TSFTHF.P.VSPARASTTH-........M.TA.....I..........QSF.KVLV..DQRLSHNL.NN.DT.KSLK.Q....  92
EChP28    ..Y..VF..S......IS.L.GV....PA-GSGIN-.........M..A..........V........QN....A.SNSSPN.V...S......  92
OMP-1B    ..Y...FVSS.....SIL.YQ..A.PVTSNDT.INDSREG.....V..N..I..RK...E.APINGNTSI.KK........K------GDIAQSAN.NRTDPAL..  97
OMP-1C    ....FF.....ALP.SFL.G.LL.EPV..DSVS-...........M..A.....V...........KNP..ALY....Q..N.-VSASSHADAD.NNKG...  92
OMP-1D    ...E.FF.....TL..SFI.G..L..PV..D.IS-...........M..A.....V...........RNT..............IEQ...RCV.SKTTLS.I...  93
OMP-1E    ....EF.......V...SFI.G......PV.GD.IS-.........M..A...M.............KNP..ALY....Q..E.-ISSSHNDNH.NNKG...  92
OMP-1F    ....FF..T.V..SFL.G......AV.ND.V.-.............V......Q--.............RNT.T...........Q........T.S.SPENT.N......  93
MAP-1     .....F..ST...VSFL.GV......V..EE.NPV.S----.V...A..M.TA...KM.I.------D.RD.KA......K....VKTPSGNTNSI..EKD..  94
                                    VR1                                                        VR2

EC28-1    RYENNPFLGFAGAIGYSMGGPRIEFEISYEAFDVKSPNINYQNDA-HRYCALSH------HTSAAME----ADKFVLKNEGLIDISLAINACYDIINDKVP  183
EC28SA2   K.AS.K......V..........I.S...VM.....N.GD..K.G..-Y............QDD.DDDMTSAT....Y.I....LN..FMT.I..ETASKNI.  188
EC28SA1   K.K.............I.NS...LV.H.I..T.N.GN..L..S--..K.......GSHICSDGNSGDWYTAKT......L.........L.V..FML......TTE.M..  193
EChP28    K...............D......L.V...T......NQGN..K.E.-.........NS.ADMSSASNN...........ADK.Y.V....L....FML.......VVGEGI..  185
OMP-1B    EFQ..LIS..S.S...A.D.....I.AA.QK..A.N.DN.DT.SGDYYK..FG..REDAI---------ADK.Y.V....ITFM..MV.T......TAEG...  188
OMP-1C    K......................V....T.......NQGG...K......-...........DR-----KA.ST.-NAT.SHY.L.......L....ML.......VVSEGI..  184
OMP-1D    K.....L.S.............D.....L.V......NQGN...K.E.---..Y.............LLGTETQIDGAGSAS.....I.....L.K.FML.....V.SEGI..  188
OMP-1E    K.............V..L.N......L.V......T......NQGN...K........GQ-----QDNSG---IPKTS.Y.L..S....L..FML.........ML....V.SEGI..  184
OMP-1F    K................V......N.......T.......RN.GG..K...........M........-.....K.Y.T.-----NSGGKLSNAG..........L....ML.........ESI..  186
MAP-1     K....................V...........V...........K..V......K..ATSKVFTS.GNASSAVSPGF.SAI.D......II...V.....ML.GM..  185
                                    VR3

EC28-1    VSPYICAGIGTDLISMFEATSPKISYQGKLGISYSINPETSVFIGGHFHRIIGNEFRDIPA---IVPSNSTTISGPQF-ATVTLNVCHFGLELGGRFNF  278
EC28SA2   L......H.....T.H........IA.FVSA.S..SF.IY..K..N.K.KNV.....-...Y.........C.....  283
EC28SA1   F............T.QN.......LN.T..SRV...A......KV......KG..T--LL.DG.NIKVQQS--........D.....I.S..F....  287
EChP28    F.......V......N.........L.....S...A.........KV..........T-----.I..TG..LAGKGNYP.I.I.D.....I.....A....  281
OMP-1B    FI.A..V.A...NV..KDFNL.F.......I...PT.V.A....YY.GV..N.NK..VITPV..LEGAPQTTS-----L..IDTGY..G.V.V...T....  283
OMP-1C    F........V......IN.........L..........A....V........KVA..........ST-----LKAFATPSSAATPDL....S.....V.........  280
OMP-1D    F........I..V.....IN.........L..P.S..A.............KV........T-----MI..E.ALAGKGNYP.I..D.FY..I........QL  286
OMP-1E    L........V......IN.........N..............A........KV........T-----LKAFVTSS--ATPDL.I....S.............I........  278
OMP-1F    F........V......IN........S..A......V...........KV...........-----MI..T..LTGN-H.-TI....S..........V......  280
MAP-1     ........V......V.VIN..N..L.........A.I..............V......K..ATSKVFTS.GNASSAVSPGF.SAI.D......II...V.....  284
                                    VR4

Fig. 3
```

Eca28SA2

```
ATGAATTGTAAAAAAGTTTTCACAATAAGTGCATTGATATCATCCATATACTTCCTACCT    60
 M  N  C  K  K  V  F  T  I  S  A  L  I  S  S  I  Y  F  L  P

AATGTCTCATACTCTAACCCAGTATATGGTAACAGTATGTATGTTAATTTTTACATATCA   120
 N  V  S  Y  S  N  P  V  Y  G  N  S  M  Y  G  N  F  Y  I  S

GGAAAGTACATGCCAAGTGTTCCTCATTTTGGAATTTTTCAGCTGAAGAAGAGAAAAAA    180
 G  K  Y  M  P  S  V  P  H  F  G  I  F  S  A  E  E  E  K  K

AAGACAACTGTAGTATATGGCTTAAAAGAAAACTGGGCAGGAGATGCAATATCTAGTCAA   240
 K  T  T  V  V  Y  G  L  K  E  N  W  A  G  D  A  I  S  S  Q

AGTCCAGATGATAATTTTACCATTCGAAATTACTCATTCAAGTATGCAAGCAACAAGTTT   300
 S  P  D  D  N  F  T  I  R  N  Y  S  F  K  Y  A  S  N  K  F

TTAGGGTTTGCAGTAGCTATTGGTTACTCGATAGGCAGTCCAAGAATAGAAGTTGAGATG   360
 L  G  F  A  V  A  I  G  Y  S  I  G  S  P  R  I  E  V  E  M

TCTTATGAAGCATTTGATGTGAAAAATCCAGGTGATAATTACAAAAACGGTGCTTACAGG   420
 S  Y  E  A  F  D  V  K  N  P  G  D  N  Y  K  N  G  A  Y  R

TATTGTGCTTTATCTCATCAAGATGATGCGGATGATGACATGACTAGTGCAACTGACAAA   480
 Y  C  A  L  S  H  Q  D  D  A  D  D  D  M  T  S  A  T  D  K

TTTGTATATTAATTAATGAAGGATTACTTAACATTCATTTATGACAAACATATGTTAT    540
 F  V  Y  L  I  N  E  G  L  L  N  I  S  F  M  T  N  I  C  Y

GAAACAGCAAGCAAAAATATACCTCTCTCCTTACATATGTGCAGGTATTGGTACTGAT    600
 E  T  A  S  K  N  I  P  L  S  P  Y  I  C  A  G  I  G  T  D

TTAATTCACATGTTTGAAACTACACATCCTAAAATTTCTTATCAAGGAAAGCTAGGGTTG   660
 L  I  H  M  F  E  T  T  H  P  K  I  S  Y  Q  G  K  L  G  L
```

Fig. 7A

```
GCCTACTTCGTAAGTGCAGAGTCTTCGGTTTCTTTTGTATATATTTCATAAAATTATA   720
 A  Y  F  V  S  A  E  S  S  V  S  F  G  I  Y  F  H  K  I  I

AATAATAAGTTTAAAAAATGTTCCAGCCATGGTACCTATTAACTCAGACGAGATAGTAGGA   780
 N  N  K  F  K  N  V  P  A  M  V  P  I  N  S  D  E  I  V  G

CCACAGTTTGCAACAGTAACATTAAATGTATGCTACTTTGGATTAGAACTTGGATGTAGG   840
 P  Q  F  A  T  V  T  L  N  V  C  Y  F  G  L  E  L  G  C  R
                   (SEQ ID NO: 3)
TTCAACTTCTAAATTCGTGGTACACATATCACGAAGCTAAAAATTGTTTTTTTATCTCTGC   900
 F  N  F  *  (SEQ ID NO: 4)

TGTATACAAGAGAAAAAATAGTAGTGAAAAATTACCTAACAATATGACAGTACAAGTTAC   960
CAAGCTTATTCTCCACAAACTTCTGTGTTTATCTCTTTATCAATGAAATGTACACTT    1020
AGCTTCACTACTGTAGAGTGTGTTTATCAATGCTTTGTTTATTAATACTCTACATAATAT  1080
GTTAAATTTTTTCTTACAAAACTCACTAGTAATTTATACTAGAATATATATTCTGACTTGT 1140
                                                (SEQ ID NO: 31)
ECa28SA3
ATTTGCTTTATACTTCCACTATTGTTAATTTATTTTCACTATTTTAGGTGTAATATGAAT  1200
                                                         M  N

TGCAAAAAATTCTTATAACAACTGCATTAATGTCATTAATGTACTATGCTCCAAGCATA   1260
 C  K  K  I  L  I  T  T  A  L  M  S  L  M  Y  Y  A  P  S  I

TCTTTTTCTGATACTATACAAGACGATAACACTGGTAGCTTCTACATCAGTGGAAAATAT  1320
 S  F  S  D  T  I  Q  D  D  N  T  G  S  F  Y  I  S  G  K  Y

GTACCAAGTGTTTCACATTTTGGTGTTTTCTCAGCTAAAGAAGAAAGAAACTCAACTGTT  1380
 V  P  S  V  S  H  F  G  V  F  S  A  K  E  E  R  N  S  T  V

GGAGTTTTTGGATTAAAACATGATTGGAATGGAGGTACAATATCTAACTCTTCTCCAGAA  1440
 G  V  F  G  L  K  H  D  W  N  G  G  T  I  S  N  S  S  P  E
```

Fig. 7B

```
AATATATTCACAGTTCAAAATTATTCGTTTAAATACGAAAACAACCCATTCTTAGGGTTT  1500
 N  I  F  T  V  Q  N  Y  S  F  K  Y  E  N  N  P  F  L  G  F
GCAGGAGCTATTGGTTATTCAATGGGTGGCCCAAGAATAGAACTTGAAGTTCTGTACGAG  1560
 A  G  A  I  G  Y  S  M  G  G  P  R  I  E  L  E  V  L  Y  E
ACATTCGATGTGAAAAATCAGAACAATAATTATAAGAACGGCGCACACAGATACTGTGCT  1620
 T  F  D  V  K  N  Q  N  N  N  Y  K  N  G  A  H  R  Y  C  A
TTATCTCATCATAGTTCAGCAACAAGCATGTCCTCCCGCAAGTAACACAAATTTGTTTCTTA  1680
 L  S  H  H  S  A  T  S  M  S  S  A  S  N  K  F  V  F  L
AAAAATGAAGGGTTAATTGACTTATCATTTATGATAAATGCATGCTATGACATAATAATT  1740
 K  N  E  G  L  I  D  L  S  F  M  I  N  A  C  Y  D  I  I  I
GAAGGAATGCCTTTTCACCTTTATATTTGTGCAGGTGTTGGTACTGATGTGTTCCATG  1800
 E  G  M  P  F  S  P  Y  I  C  A  G  V  G  T  D  V  V  S  M
TTTGAAGCTATAAATCCTAAAATTTCTTACCAAGGAAAACTAGGATTAGGTTATAGTATA  1860
 F  E  A  I  N  P  K  I  S  Y  Q  G  K  L  G  L  G  Y  S  I
AGTTCAGAAGCCTCTGTTTTTATCGGTGGACACTTTCACAGAGTCATAGGTAATGAATTT  1920
 S  S  E  A  S  V  F  I  G  G  H  F  H  R  V  I  G  N  E  F
AGAGACATCCCTGCTATGGTTCCTAGTGGATCAAATCTTCCAGAAAACCAATTTGCAATA  1980
 R  D  I  P  A  M  V  P  S  G  S  N  L  P  E  N  Q  F  A  I    (SEQ ID NO: 5)
GTAACACTAAATGTGTGTCACTTTGGCATAGAACTTGGAGGAAGATTTAACTTCTGA  2031
 V  T  L  N  V  C  H  F  G  I  E  L  G  G  R  F  N  F  *       (SEQ ID NO: 6)
```

HOMOLOGOUS 28-KILODALTON IMMUNODOMINANT PROTEIN GENES OF *EHRLICHIA CANIS* AND USES THEREOF

CROSS-REFERENCE TO RELATED APPLICATION

This patent application is a continuation-in-part of U.S. application Ser. No. 09/201,458, filed Nov. 30, 1998.

BACKGROUND OF THE INVENTION

1. Field of the Invention

The present invention relates generally to the field of molecular biology. More specifically, the present invention relates to molecular cloning and characterization of homologous 28-kDa protein genes in *Ehrlichia canis* and a multigene locus encoding the 28-kDa homologous proteins of *Ehrlichia canis* and uses thereof.

2. Description of the Related Art

Canine ehrlichiosis, also known as canine tropical pancytopenia, is a tick-borne rickettsial disease of dogs first described in Africa in 1935 and the United States in 1963 (Donatien and Lestoquard, 1935; Ewing, 1963). The disease became better recognized after an epizootic outbreak occurred in United States military dogs during the Vietnam War (Walker et al., 1970)

The etiologic agent of canine ehrlichiosis is *Ehrlichia canis*, a small, gram-negative, obligate intracellular bacterium which exhibits tropism for mononuclear phagocytes (Nyindo et al., 1971) and is transmitted by the brown dog tick, *Rhipicephalus sanguineus* (Groves et al., 1975). The progression of canine ehrlichiosis occurs in three phases, acute, subclinical and chronic. The acute phase is characterized by fever, anorexia, depression, lymphadenopathy and mild thrombocytopenia (Troy and Forrester, 1990). Dogs typically recover from the acute phase, but become persistently infected carriers of the organism without clinical signs of disease for months or even years (Harrus et al., 1998). A chronic phase develops in some cases that is characterized by thrombocytopenia, hyperglobulinemia, anorexia, emaciation, and hemorrhage, particularly epistaxis, followed by death (Troy and Forrester, 1990).

Molecular taxonomic analysis based on the 16S rRNA gene has determined that *E. canis* and *E. chaffeensis*, the etiologic agent of human monocytic ehrlichiosis (HME), are closely related (Anderson et al., 1991; Anderson et al., 1992; Dawson et al., 1991; Chen et al., 1994). Considerable cross reactivity of the 64, 47, 40, 30, 29 and 23-kDa antigens between *E. canis* and *E. chaffeensis* has been reported (Chen et al., 1994; Chen et al., 1997; Rikihisa et al., 1994; Rikihisa et al., 1992). Analysis of immunoreactive antigens with human and canine convalescent phase sera by immunoblot has resulted in the identification of numerous immunodominant proteins of *E. canis*, including a 30-kDa protein (Chen et al., 1997). In addition, a 30-kDa protein of *E. canis* has been described as a major immunodominant antigen recognized early in the immune response that is antigenically distinct from the 30-kDa protein of *E. chaffeensis* (Rikihisa et al., 1992; Rikihisa et al., 1994). Other immunodominant proteins of *E. canis* with molecular masses ranging from 20 to 30-kDa have also been identified (Brouqui et al., 1992; Nyindo et al., 1991; Chen et al., 1994; Chen et al., 1997).

Recently, cloning and sequencing of a multigene family (omp-1) encoding proteins of 23 to 28-kDa have been described for *E. chaffeensis* (Ohashi et al., 1998). The 28-kDa immunodominant outer membrane protein gene (p28) of *E. chaffeensis*, homologous to the *Cowdria ruminantium* map-1 gene, was cloned. Mice immunized with recombinant P28 were protected against challenge infection with the homologous strain according to PCR analysis of periperal blood 5 days after challenge (Ohashi et al., 1998). Molecular cloning of two similar, but nonidentical, tandemly arranged 28-kDa genes of *E. canis* homologous to *E. chaffeensis* omp-1 gene family and *C. rumanintium* map-1 gene has also been reported (Reddy et al., 1998).

The prior art is deficient in the lack of cloning and characterization of new homologous 28-kDa immunoreactive protein genes of *Ehrlichia canis* and a single multigene locus containing the homologous 28-kDa protein genes. Further, The prior art is deficient in the lack of recombinant proteins of such immunoreactive genes of *Ehrlichia canis*. The present invention fulfills this long-standing need and desire in the art.

SUMMARY OF THE INVENTION

The present invention describes the molecular cloning, sequencing, characterization, and expression of homologous mature 28-kDa immunoreactive protein genes of *Ehrlichia canis* (designated Eca28-1, ECa28SA3 and ECa28SA2), and the identification of a single locus (5.592-kb) containing five 28-kDa protein genes of *Ehrlichia canis* (ECa28SA1, ECa28SA2, ECa28SA3, Eca28-1 and ECa28-2). Comparison with *E. chaffeensis* and among *E. canis* 28-kDa protein genes revealed that ECa28-1 shares the most amino acid homology with the *E. chaffeensis* omp-1 multigene family and is highly conserved among *E. canis* isolates. The five 28-kDa proteins were predicted to have signal peptides resulting in mature proteins, and had amino acid homology ranging from 51 to 72%. Analysis of intergenic regions revealed hypothetical promoter regions for each gene, suggesting that these genes may be independently and differentially expressed. Intergenic noncoding regions ranged in size from 299 to 355-bp, and were 48 to 71% homologous.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, SEQ ID No. 4 and SEQ ID No. 6, and the gene has a nucleic acid sequence selected from the group consisting of SEQ ID No. 1, SEQ ID No. 3 and SEQ ID No. 5 and is a member of a polymorphic multiple gene family. Generally, the protein has an N-terminal signal sequence which is cleaved after post-translational process resulting in the production of a mature 28-kDa protein. Still preferably, the DNAs encoding 28-kDa proteins are contained in a single multigene locus, which has the size of 5.592 kb and encodes all five homologous 28-kDa proteins of *Ehrlichia canis*.

In another embodiment of the present invention, there is provided an expression vector comprising a gene encoding a 28-kDa immunoreactive protein of *Ehrlichia canis* and capable of expressing the gene when the vector is introduced into a cell.

In still another embodiment of the present invention, there is provided a recombinant protein comprising an amino acid sequence selected from the group consisting of SEQ ID No. 2, SEQ ID No. 4 and SEQ ID No. 6. Preferably, the amino acid sequence is encoded by a nucleic acid sequence selected from the group consisting of SEQ ID No. 1, SEQ ID No. 3 and SEQ ID No. 5. Preferably, the recombinant protein comprises four variable regions which are surface exposed, hydrophilic and antigenic. The recombinant protein may be useful as an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID No. 2, SEQ ID No. 4 and SEQ ID No. 6 operatively linked to a promoter; transfecting the vector into a cell; and culturing the cell under conditions effective for expression of the expression region.

The invention may also be described in certain embodiments as a method of inhibiting *Ehrlichia canis* infection in a subject comprising the steps of: identifying a subject suspected of being exposed to or infected with *Ehrlichia canis*; and administering a composition comprising a 28-kDa antigen of *Ehrlichia canis* in an amount effective to inhibit an *Ehrlichia canis* infection. The inhibition may occur through any means such as, i.e. the stimulation of the subject's humoral or cellular immune responses, or by other means such as inhibiting the normal function of the 28-kDa antigen, or even competing with the antigen for interaction with some agent in the subject's body.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B show nucleic acid sequence (SEQ ID No. 1) and deduced amino acid sequence (SEQ ID No. 2) of ECa28-1 gene including adjacent 5' and 3' non-coding sequences. The ATG start codon and TAA termination are shown in bold, and the 23 amino acid leader signal sequence is underlined.

FIG. 3 shows alignment of ECa28-1 protein (SEQ ID NO. 2), and ECa28SA2 (partial sequence, SEQ ID NO. 7) and ECa28SA1 (SEQ ID NO. 8), *E. chaffeensis* P28 (SEQ ID NO. 9), *E. chaffeensis* OMP-1 family (SEQ ID NOs: 10–14) and *C. ruminantium* MAP-1 (SEQ ID NO. 15) amino acid sequences. The ECa28-1 amino acid sequence is presented as the consensus sequence. Amino acids not shown are identical to ECa28-1 and are represented by a dot. Divergent amino acids are shown with the corresponding one letter abbreviation. Gaps introduced for maximal alignment of the amino acid sequences are denoted with a dash. Variable regions are underlined and denoted (VR1, VR2, VR3, and VR4). The arrows indicate the predicted signal peptidase cleavage site for the signal peptide.

FIGS. 7A–7C show nucleic acid sequences and deduced amino acid sequences of the *E. canis* 28-kDa protein genes ECa28SA2 (nucleotide 1–849: SEQ ID No. 3; amino acid sequence: SEQ ID No. 4) and ECa28SA3 (nucleotide 1195–2031: SEQ ID No. 5; amino acid sequence: SEQ ID No. 6) including intergenic noncoding sequences (NC2, nucleotide 850–1194: SEQ ID No. 31). The ATG start codon and termination codons are shown in bold.

FIG. 10 shows alignment of *E. canis* 28-kDa protein gene intergenic noncoding nucleic acid sequences (SEQ ID Nos. 30–33). Nucleic acids not shown, denoted with a dot (.), are identical to noncoding region 1 (28NC1). Divergence is shown with the corresponding one letter abbreviation. Gaps introduced for maximal alignment of the amino acid sequences are denoted with a dash (-). Putative transcriptional promoter regions (-10 and -35) and ribosomal binding site (RBS) are boxed.

DETAILED DESCRIPTION OF THE INVENTION

Figure 2:
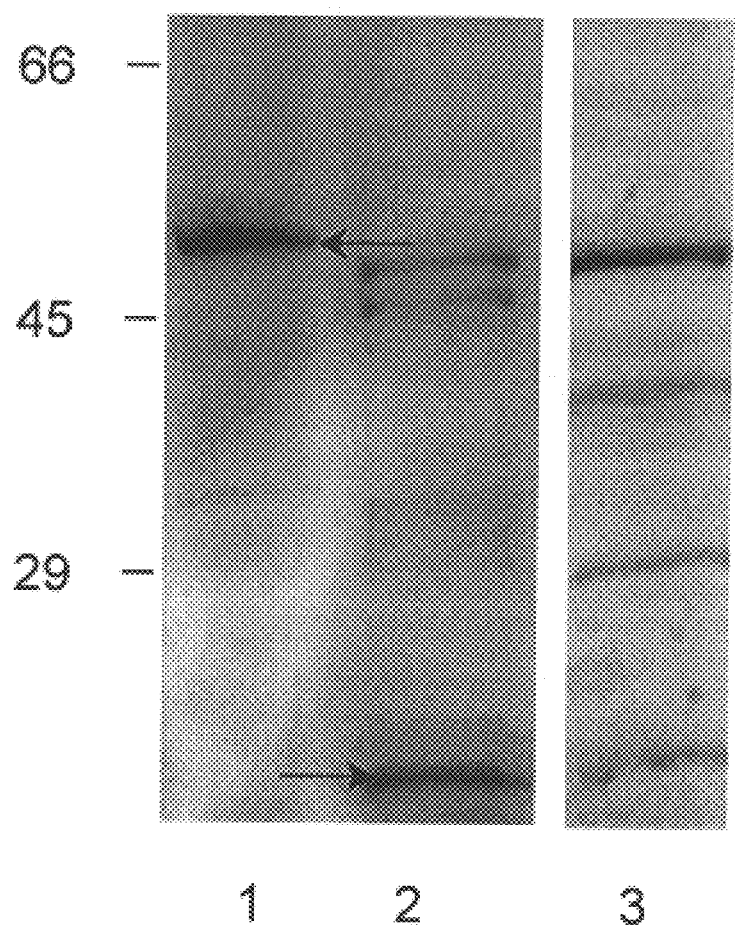
FIG. 2 shows SDS-PAGE of expressed 50-kDa recombinant ECa28-1-thioredoxin fusion protein (Lane 1, arrow) and 16-kDa thioredoxin control (Lane 2, arrow), and corresponding immunoblot of recombinant ECa28-1-thioredoxin fusion protein recognized by covalescent-phase *E. canis* canine antiserum (Lane 3). Thiroredoxin control was not detected by *E. canis* antiserum (not shown).

The present invention describes cloning, sequencing and expression of homologous genes encoding a 30-kilodalton (kDa) protein of *Ehrlichia canis*. A comparative molecular analysis of homologous genes among seven *E. canis* isolates and the *E. chaffeensis* omp-1 multigene family was also performed. Two new 28-kDa protein genes are identified, ECa28-1 and ECa28SA3. ECa28-1 has an 834-bp open reading frame encoding a protein of 278 amino acids (SEQ ID No. 2) with a predicted molecular mass of 30.5-kDa. An N-terminal signal sequence was identified suggesting that the protein is post-translationally modified to a mature protein of 27.7-kDa. ECa28SA3 has an 840-bp open reading frame encoding a 280 amino acid protein (SEQ ID No. 6).

Using PCR to amplify 28-kDa protein genes of *E. canis*, a previously unsequenced region of Eca28SA2 was completed. Sequence analysis of ECa28SA2 revealed an 849-bp open reading frame encoding a 283 amino acid protein (SEQ ID No. 4). PCR amplification using primers specific for 28-kDa protein gene intergenic noncoding regions linked two previously separate loci, identifying a single locus (5.592-kb) containing all five 28-kDa protein genes. The five 28-kDa proteins were predicted to have signal peptides resulting in mature proteins, and had amino acid homology ranging from 51 to 72%. Analysis of intergenic regions revealed hypothetical promoter regions for each gene, suggesting that these genes may be independently and differentially expressed. Intergenic noncoding regions (28NC1-4) ranged in size from 299 to 355-bp, and were 48 to 71% homologous.

The present invention is directed to two new homologous 28-kDa protein genes in *Ehrlichia canis*, Eca28-1 and ECa28SA3, and a complete sequence of previously partially sequenced ECa28SA2. Also disclosed is a multigene locus encoding all five homologous 28-kDa outer membrane proteins of *Ehrlichia canis*.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, SEQ ID No. 4 and SEQ ID No. 6, and the gene has a nucleic acid sequence selected from the group consisting of SEQ ID No. 1, SEQ ID No. 3 and SEQ ID No. 5 and is a member of a polymorphic multiple gene family. More preferably, the protein has an N-terminal signal sequence which is cleaved after post-translational process resulting in the production of a mature 28-kDa protein. Still preferably, the DNAs encoding 28-kDa proteins are contained in a single multigene locus, which has the size of 5.592 kb and encodes all five homologous 28-kDa proteins of *Ehrlichia canis*.

In another embodiment of the present invention, there is provided an expression vector comprising a gene encoding a 28-kDa immunoreactive protein of *Ehrlichia canis* and capable of expressing the gene when the vector is introduced into a cell.

In still another embodiment of the present invention, there is provided a recombinant protein comprising an amino acid sequence selected from the group consisting of SEQ ID No. 2, SEQ ID No. 4 and SEQ ID No. 6. Preferably, the amino acid sequence is encoded by a nucleic acid sequence selected from the group consisting of SEQ ID No. 1, SEQ ID No. 3 and SEQ ID No. 5. Preferably, the recombinant protein comprises four variable regions which are surface exposed, hydrophilic and antigenic. Still preferably, the recombinant protein is an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID No. 2, SEQ ID No. 4 and SEQ ID No. 6 operatively linked to a promoter; transfecting the vector into a cell; and culturing the cell under conditions effective for expression of the expression region.

The invention may also be described in certain embodiments as a method of inhibiting *Ehrlichia canis* infection in a subject comprising the steps of: identifying a subject suspected of being exposed to or infected with *Ehrlichia canis*; and administering a composition comprising a 28-kDa antigen of *Ehrlichia canis* in an amount effective to inhibit an *Ehrlichia canis* infection. The inhibition may occur through any means such as, i.e. the stimulation of the subject's humoral or cellular immune responses, or by other means such as inhibiting the normal function of the 28-kDa antigen, or even competing with the antigen for interaction with some agent in the subject's body.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes a 28-kDa immunoreactive protein of *Ehrlichia canis* of the present invention can be used to transform a host using any of the techniques commonly known to those of ordinary skill in the art. Especially preferred is the use of a vector containing coding sequences for a gene encoding a 28-kDa immunoreactive protein of *Ehrlichia canis* of the present invention for purposes of prokaryote transformation.

Prokaryotic hosts may include *E. coli, S. tymphimurium, Serratia marcescens* and *Bacillus subtilis.* Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a 28-kDa immunoreactive protein of *Ehrlichia canis,* a strand of which DNA will hybridize at high stringency to a probe containing a sequence of at least 15 consecutive nucleotides of SEQ ID No. 1 or SEQ ID No. 3 or SEQ ID No. 5. The protein encoded by the DNA of this invention may share at least 80% sequence identity (preferably 85%, more preferably 90%, and most preferably 95%) with the amino acids listed in SEQ ID No. 2 or SEQ ID No. 4 or SEQ ID No. 6. More preferably, the DNA includes the coding sequence of the nucleotides of SEQ ID No. 1 or SEQ ID No. 3 or SEQ ID No. 5, or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID No. 1 or SEQ ID No. 3 or SEQ ID No. 5 or the complement thereof. Such a probe is useful for detecting expression of the 28-kDa immunoreactive protein of *Ehrlichia canis* in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from the nucleotides listed in SEQ ID No 1 or SEQ ID No.3 or SEQ ID No.5.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID No. 1 or SEQ ID No. 3 or SEQ ID No. 5 which encodes an alternative splice variant of a gene encoding a 28-kDa immunoreactive protein of *Ehrlichia canis.*

The DNA may have at least about 70% sequence identity to the coding sequence of the nucleotides listed in SEQ ID No.1 or SEQ ID No. 3 or SEQ ID No. 5, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence coding for a which encodes a gene encoding a 28-kDa immunoreactive protein of *Ehrlichia canis* and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No. 1 or SEQ ID No. 3 or SEQ ID No. 5.

A "vector" may be defined as a replicable nucleic acid construct, e.g., a plasmid or viral nucleic acid. Vectors may be used to amplify and/or express nucleic acid encoding a 28-kDa immunoreactive protein of *Ehrlichia canis.* An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure 28-kDa immunoreactive protein of *Ehrlichia canis* may be obtained, for example, by extraction from a natural source; by expression of a recombinant nucleic acid encoding a 28-kDa immunoreactive protein of *Ehrlichia canis*; or by chemically synthesizing the protein. Purity can be measured by any appropriate method, e.g., column chromatography such as immunoaffinity chromatography using an antibody specific for a 28-kDa immunoreactive protein of *Ehrlichia canis*, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the 28-kDa immunoreactive protein of *Ehrlichia canis* (SEQ ID No. 2 or SEQ ID No. 4 or SEQ ID No. 6). As used herein, "fragment," as applied to a polypeptide, will ordinarily be at least 10 residues, more typically at least 20 residues, and preferably at least 30 (e.g., 50) residues in length, but less than the entire, intact sequence. Fragments of the 28-kDa immunoreactive protein of *Ehrlichia canis* can be generated by methods known to those skilled in the art, e.g., by enzymatic digestion of naturally occurring or recombinant 28-kDa immunoreactive protein of *Ehrlichia canis*, by recombinant DNA techniques using an expression vector that encodes a defined fragment of 28-kDa immunoreactive protein of *Ehrlichia canis*, or by chemical synthesis. The ability of a candidate fragment to exhibit a characteristic of 28-kDa immunoreactive protein of *Ehrlichia canis* (e.g., binding to an antibody specific for 28-kDa immunoreactive protein of *Ehrlichia canis*) can be assessed by methods described herein. Purified 28-kDa immunoreactive protein of *Ehrlichia canis* or antigenic fragments of 28-kDa immunoreactive protein of *Ehrlichia canis* can be used to generate new antibodies or to test existing antibodies (e.g., as positive controls in a diagnostic assay) by employing standard protocols known to those skilled in the art. Included in this invention are polyclonal antisera generated by using 28-kDa immunoreactive protein of *Ehrlichia canis* or a fragment of 28-kDa immunoreactive protein of *Ehrlichia canis* as the immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia canis* cDNA clones, and to distinguish them from known cDNA clones.

Further included in this invention are fragments of the 28-kDa immunoreactive protein of *Ehrlichia canis* which are encoded at least in part by portions of SEQ ID No. 1 or SEQ ID No. 3 or SEQ ID No. 5, e.g., products of alternative mRNA splicing or alternative protein processing events, or in which a section of the sequence has been deleted. The fragment, or the intact 28-kDa immunoreactive protein of *Ehrlichia canis*, may be covalently linked to another polypeptide, e.g. which acts as a label, a ligand or a means to increase antigenicity.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others.

Means for conjugating a polypeptide to a carrier protein are well known in the art and include glutaraldehyde, m-maleimidobenzoyl-N-hydroxysuccinimide ester, carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

As used herein, the term "engineered" or "recombinant" cell is intended to refer to a cell into which a recombinant gene, such as a gene encoding an Ehrlichia chaffeensis antigen has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

The following examples are given for the purpose of illustrating various embodiments of the invention and are not meant to limit the present invention in any fashion.

EXAMPLE 1

Ehrlichiae and Purification

*Ehrlichia canis* (Florida strain and isolates Demon, DJ, Jake, and Fuzzy) were provided by Dr. Edward Breitschwerdt, (College of Veterinary Medicine, North Carolina State University, Raleigh, N.C.). *E. canis* (Louisiana strain) was provided by Dr. Richard E. Corstvet (School of Veterinary Medicine, Louisiana State University, Baton Rouge, La.) and *E. canis* (Oklahoma strain) was provided by Dr. Jacqueline Dawson (Centers for Disease Control and Prevention, Atlanta, Ga.). Propagation of Ehrlichiae was performed in DH82 cells with DMEM supplemented with 10% bovine calf serum and 2 mM L-glutamine at 37° C. The intracellular growth in DH82 cells was monitored by presence of *E. canis* morulae using general cytologic staining methods. Cells were harvested when 100% of the cells were infected with Ehrlichiae and were then pelleted in a centrifuge at 17,000×g for 20 min. Cell pellets were disrupted with a Braun-Sonic 2000 sonicator twice at 40W for 30 sec on ice. Ehrlichiae were purified as described previously (Weiss et al., 1975). The lysate was loaded onto discontinuous gradients of 42%–36%–30% renografin, and centrifuged at 80,000×g for 1 hr. Heavy and light bands containing Ehrlichiae were collected and washed with sucrose-phosphate-glutamate buffer (SPG, 218 mM sucrose, 3.8 mM $KH_2PO_4$, 7.2 mM $K_2HPO_4$, 4.9 mM glutamate, pH 7.0) and pelleted by centrifugation.

EXAMPLE 2

Nucleic Acid Preparation

*Ehrlichia canis* genomic DNA was prepared by resuspending the renografin-purified Ehrlichiae in 600 µl of 10 mM Tris-HCl buffer (pH 7.5) with 1% sodium dodecyl sulfate (SDS, w/v) and 100 ng/ml of proteinase K as described previously (McBride et al., 1996). This mixture was incubated for 1 hr at 56° C., and the nucleic acids were extracted twice with a mixture of phenol/chloroform/isoamyl alcohol (24:24:1). DNA was pelleted by absolute ethanol precipitation, washed once with 70% ethanol, dried and resuspended in 10 mM Tris (pH 7.5). Plasmid DNA was purified by using High Pure Plasmid Isolation Kit (Boehringer Mannheim, Indianapolis, Ind.), and PCR products were purified using a QIAquick PCR Purification Kit (Qiagen, Santa Clarita, Calif.).

EXAMPLE 3

PCR Amplification of the *E. canis* 28-kDa Protein Genes

Regions of the *E. canis* ECa28-1 gene selected for PCR amplification were chosen based on homology observed (>90%) in the consensus sequence generated from Jotun-Hein aligorithm alignment of *E. chaffeensis* p28 and *Cowdria ruminantium* map-1 genes. Forward primer 793 (5-GCAGGAGCTGTTGGTTACTC-3') (SEQ ID NO. 16) and reverse primer 1330 (5'-CCTTCCTCCAAGTTCTATGCC-3') (SEQ ID NO. 17) corresponded to nucleotides 313–332 and 823–843 of *C. ruminantium* MAP-1 and 307–326 and 834–814 of *E. chaffeensis* P28. *E. canis* (a North Carolina isolate, Jake) DNA was amplified with primers 793 and 1330 with a thermal cycling profile of 95° C. for 2 min, and 30 cycles of 95° C. for 30 sec, 62° C. for 1 min, 72° C. for 2 min followed by a 72° C. extension for 10 min and 4° C. hold. PCR products were analyzed on 1% agarose gels. This amplified PCR product was sequenced directly with primers 793 and 1330.

Primers specific for ECa28SA2 gene designated 46f (5'-ATATACTTCCTACCTAATGTCTCA-3', SEQ ID No. 18) and primer 1330 (SEQ ID No. 17) were used to amplify the targeted region. The amplified product was gel purified and cloned into a TA cloning vector (Invitrogen, Santa Clarita, Calif.). The clone was sequenced bidirectionally with primers: M13 reverse from the vector, 46f, ECa28SA2 (5'-AGTGCAGAGTCTTCGGTTTC-3', SEQ ID No. 19), ECa5.3 (5'-GTTACTTGCGGAGGACAT-3', SEQ ID No. 20). DNA was amplified with a thermal cycling profile of 95° C. for 2 min, and 30 cycles of 95° C. for 30 sec, 48° C. for 1 min, 72° C. for 1 min followed by a 72° C. extension for 10 min and 4° C. hold.

EXAMPLE 4

Sequencing Unknown 5' and 3' Regions of the ECa28-1 Gene

The full length sequence of ECa28-1 was determined using a Universal GenomeWalker Kit (CLONECH, Palo Alto, Calif.) according to the protocol supplied by the manufacturer. Genomic *E. canis* (Jake isolate) DNA was digested completely with five restriction enzymes (DraI, EcoRV, PvuII, ScaI, StuI) which produce blunt-ended DNA. An adapter (AP1) supplied in the kit was ligated to each end of *E. canis* DNA. The genomic libraries were used as templates to find the unknown DNA sequence of the ECa28-1 gene by PCR using a primer complementary to a known portion of the ECa28-1 sequence and a primer specific for the adapter AP1. Primers specific for ECa28-1 used for genome walking were designed from the known DNA sequence derived from PCR amplification of ECa28-1 with primers 793 (SEQ ID NO. 16) and 1330 (SEQ ID NO. 17). Primers 394 (5'-GCATTTCCACAGGATCATAGGTAA-3'; nucleotides 687–710, SEQ ID NO. 21) and 394C (5'-TTACCTATGATCCTGT GGAAATGC-3; nucleotides 710–687, SEQ ID NO. 22) were used in conjunction with supplied primer AP1 to amplify the unknown 5' and 3' regions of the ECa28-1 gene by PCR. A PCR product corresponding to the 5' region of the ECa28-1 gene amplified with primers 394C and AP1 (2000-bp) was sequenced unidirectionally with primer 793C (5'-GAGTA ACCAACAGCTCCTGC-3', SEQ ID No. 23). A PCR product corresponding to the 3' region of the ECa28-1 gene amplified with primers 394 and AP1 (580-bp) was sequenced bidirectionally with the same primers. Noncoding regions on the 5' and 3' regions adjacent to the open reading frame were sequenced, and primers EC28OM-F (5'-TCTACTTTGCACTTCC ACTATTGT-3', SEQ ID NO. 24) and EC28OM-R (5'-ATTCTTTTGCCACTATTT TTCTTT-3', SEQ ID NO. 25) complementary to these regions were designed in order to amplify the entire ECa28-1 gene.

EXAMPLE 5

Sequencing of *E. canis* Isolates

DNA was sequenced with an AB1 Prism 377 DNA Sequencer (Perkin-Elmer Applied Biosystems, Foster City, Calif.). The entire Eca28-1 genes of seven *E. canis* isolates (four from North Carolina, and one each from Oklahoma, Florida, and Louisiana) were amplified by PCR with primers EC28OM-F (SEQ ID No. 24) and EC28OM-R (SEQ ID No. 25) with a thermal cycling profile of 95° C. for 5 minutes, and 30 cycles of 95° C. for 30 seconds, 62° C. for 1 minutes, and 72° C. for 2 minutes and a 72° C. extension for 10 minutes. The resulting PCR products were bidirectionally sequenced with the same primers.

EXAMPLE 6

Cloning and Expression of *E. canis* ECa28-1

The entire *E. canis* ECa28-1 gene was PCR-amplified with primers-EC28OM-F and EC28OM-R and cloned into pCR2.1-TOPO TA cloning vector to obtain the desired set of restriction enzyme cleavage sites (Invitrogen, Carlsbad, Calif.). The insert was excised from pCR2.1-TOPO with BstX 1 and ligated into pcDNA 3.1 eukaryotic expression vector (Invitrogen, Carlsbad, Calif.) designated pcDNA3.1/EC28 for subsequent studies. The pcDNA3.1/EC28 plasmid was amplified, and the gene was excised with a KpnI-XbaI double digestion and directionally ligated into pThioHis prokaryotic expression vector (Invitrogen, Carlsbad, Calif.). The clone (designated pThioHis/EC28) produced a recombinant thioredoxin fusion protein in *Escherichia coli* BL21. The recombinant fusion protein was crudely purified in the insoluble phase by centrifugation. The control thioredoxin fusion protein was purified from soluble cell lysates under native conditions using nickel-NTA spin columns (Qiagen, Santa Clarita, Calif.).

EXAMPLE 7

Western Immunoblot Analysis

Recombinant *E. canis* ECa28-1 fusion protein was subjected to SDS-polyacrylamide gel electrophoresis (SDS-PAGE) on 4–15% Tris-HCl gradient gels (Bio-Rad, Hercules, Calif.) and transferred to pure nitrocellulose (Schleicher & Schuell, Keene, N.H.) using a semi-dry transfer cell (Bio-Rad, Hercules, Calif.). The membrane was incubated with convalescent phase antisera from an *E. canis*-infected dog diluted 1:5000 for 1 hour, washed, and then incubated with an anti-canine IgG (H & L) alkaline phosphatase-conjugated affinity-purified secondary antibody at 1:1000 for 1 hour (Kirkegaard & Perry Laboratories, Gaithersburg, Md.). Bound antibody was visualized with 5-bromo-4-chloro-3-indolyl phosphate/nitroblue tetrazolium (BCIP/NBT) substrate (Kirkegaard & Perry Laboratories, Gaithersburg, Md.).

EXAMPLE 8

Southern Blot Analysis

To determine if multiple genes homologous to the ECa28-1 gene were present in the *E. canis* genome, a genomic Southern blot analysis was performed using a standard procedure (Sambrook et al. 1989). *E. canis* genomic DNA digested completely with each of the restriction enzymes BanII, EcoRV, HaeII, KpnI and SpeI, which do not cut within the ECa28-1 gene, and AseI which digests ECa28-1 at nucleotides 34, 43 and 656. The probe was produced by PCR amplification with primers EC28OM-F and EC28OM-R and digoxigenin (DIG)-labeled deoxynucleotide triphosphates (dNTPs) (Boehringer Mannheim, Indianapolis, Ind.) and digested with AseI. The digested probe (566-bp) was separated by agarose gel electrophoresis, gel-purified and then used for hybridization. The completely digested genomic *E. canis* DNA was electrophoresed and transferred to a nylon membrane (Boehringer Mannheim, Indianapolis, Ind.) and hybridized at 40° C. for 16 hr with the ECa28-1 gene DIG-labeled probe in DIG Easy Hyb buffer according to the manufacturer's protocol (Boehringer Mannheim, Indianapolis, Ind.). Bound probe was detected with a anti-DIG alkaline phosphatase-conjugated antibody and a luminescent substrate (Boehringer Mannheim, Indianapolis, Ind.) and exposed to BioMax scientific imaging film (Eastman Kodak, Rochester, N.Y.).

EXAMPLE 9

Sequence Analysis and Comparasion

*E. chaffeensis* p28 and *C. ruminantium* map-1 DNA sequences were obtained from the National Center of Biotechnology Information (NCBI) (World Wide Web site at URL: http://www.ncbi.nlm.nih.gov/Entrez). Nucleotide and deduced amino acid sequences, and protein and phylogenetic analyses were performed with LASERGENE software (DNASTAR, Inc., Madison, Wis.). Analysis of post-translational processing was performed by the method of McGeoch and von Heijne for signal sequence recognition using the PSORT program (McGeoch, 1985; von Heijne, 1986) (World Wide Web site at URL: PRIVATE HREF=

"http://www.imcb.osaka-u.ac.jp/nakai/form.htm", MAC-ROBUTTON HtmlResAnchor http://www.imcb.osaka-u.ac.jp/nakai/form.htm).

GenBank accession numbers for nucleic acid and amino acid sequences of the *E. canis* ECa28-1 genes described in this study are: Jake, AF082744; Louisiana, AF082745; Oklahoma, AF082746; Demon, AF082747; DJ, AF082748; Fuzzy, AF082749; Florida, AF082750.

Sequence analysis of ECa28-1 from seven different strains of *E. canis* was performed with primers designed to amplify the entire gene. Analysis revealed the sequence of this gene was conserved among the isolates from North Carolina (four), Louisiana, Florida and Oklahoma.

EXAMPLE 10

PCR Amplification, Cloning, Sequencing and Expression of ECa28-1

Alignment of nucleic acid sequences from *E. chaffeensis* p28 and *Cowdria ruminantium* map-1 using the Jotun-Hein aligorithm produced a consensus sequence with regions of high homology (>90%). These homologous regions (nucleotides 313–332 and 823–843 of *C. ruminantium* map-1; 307–326 and 814–834 of *E. chaffeensis* p28) were targeted as primer annealing sites for PCR amplification. PCR amplification of the *E. canis* ECa28-1 and *E. chaffeensis* p28 gene was accomplished with primers 793 and 1330, resulting in a 518-bp PCR product. The nucleic acid sequence of the *E. canis* PCR product was obtained by sequencing the product directly with primers 793 and 1330. Analysis of the sequence revealed an open reading frame encoding a protein of 170 amino acids, and alignment of the 518-bp sequence obtained from PCR amplification of *E. canis* with the DNA sequence of *E. chaffeensis* p28 gene revealed a similarity greater than 70%, indicating that the genes were homologous. Adapter PCR with primers 394 and 793C was performed to determine the 5' and 3' segments of the sequence of the entire gene. Primer 394 produced four PCR products (3-kb, 2-kb, 1-kb, and 0.8-kb), and the 0.8-bp product was sequenced bidirectionally using primers 394 and AP1. The deduced sequence overlapped with the 3' end of the 518-bp product, extending the open reading frame 12-bp to a termination codon. An additional 625-bp of non-coding sequence at the 31 end of the ECa28-1 gene was also sequenced. Primer 394C was used to amplify the 5' end of the ECa28-1 gene with supplied primer AP1. Amplification with these primers resulted in three PCR products (3.3, 3-kb, and 2-kb). The 2-kb fragment was sequenced unidirectionally with primer 793C. The sequence provided the putative start codon of the ECa28-1 gene and completed the 834-bp open reading frame encoding a protein of 278 amino acids. An additional 144-bp of readable sequence in the 5' non-coding region of the ECa28-1 gene was generated. Primers EC28OM-F and EC28OM-R were designed from complementary non-coding regions adjacent to the ECa28-1 gene.

The PCR product amplified with these primers was sequenced directly with the same primers. The complete DNA sequence (SEQ ID NO. 1) for the *E. canis* ECa28-1 gene is shown in FIG. 1. The ECa28-1 PCR fragment amplified with these primers contained the entire open reading frame and 17 additional amino acids from the 5' non-coding primer region. The gene was directionally subcloned into pThioHis expression vector, and *E. coli* (BL21) were transformed with this construct. The expressed ECa28-1-thioredoxin fusion protein was insoluble. The expressed protein had an additional 114 amino acids associated with the thioredoxin, 5 amino acids for the enterokinase recognition site, and 32 amino acids from the multiple cloning site and 5' non-coding primer region at the N-terminus. Convalescent-phase antiserum from an *E. canis* infected dog recognized the expressed recombinant fusion protein, but did not react with the thioredoxin control (FIG. 2).

EXAMPLE 11

Sequence Homology

The nucleic acid sequence of ECa28-1 (834-bp) and the *E. chaffeensis* omp-1 family of genes including signal sequences (ECa28-1, omp-1A, B, C, D, E, and F) were aligned using the Clustal method to examine homology between these genes (alignment not shown). Nucleic acid homology was equally conserved (68.9%) between ECa28-1, and *E. chaffeensis* p28 and omp-1F. Other putative outer membrane protein genes in the *E. chaffeensis* omp-1 family, omp-1D (68.2%), omp-1E (66.7%), omp-1C (64.1%), *Cowdria ruminantium* map-1 (61.8%), *E. canis* 28-kDa protein 1 gene (60%) and 28-kDa protein 2 gene (partial) (59.5%) were also homologous to ECa28-1. *E. chaffeensis* omp-1B had the least nucleic acid homology (45.1%) with E.Ca28-1.

Figure 4:
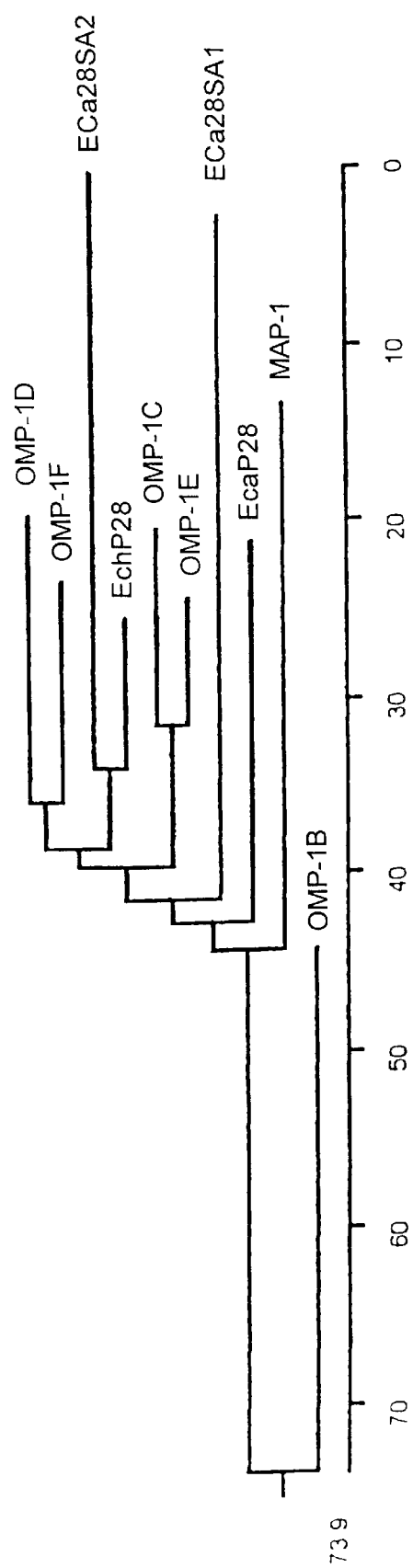
FIG. 4 shows phylogenetic relatedness of *E. canis* ECa28-1 with the ECa28SA2 (partial sequence) and ECa28SA1, 6 members of the *E. chaffeensis* omp-1 multiple gene family, and *C. rumanintium* map-1 from deduced amino acid sequences utilizing unbalanced tree construction. The length of each pair of branches represents the distance between the amino acid sequence of the pairs. The scale measures the distance between sequences.

Alignment of the predicted amino acid sequences of ECa28-1 (SEQ ID NO. 2) and *E. chaffeensis* P28 revealed amino acid substitutions resulting in four variable regions (VR). Substitutions or deletions in the amino acid sequence and the locations of variable regions of ECa28-1 and the *E. chaffeensis* OMP-1 family were identified (FIG. 3). Amino acid comparison including the signal peptide revealed that ECa28-1 shared the most homology with OMP-1F (68%) of the *E. chaffeensis* OMP-1 family, followed by *E. chaffeensis* P28 (65.5%), OMP-1E (65.1%), OMP-1D (62.9%), OMP-1C (62.9%), *Cowdria ruminantium* MAP-1 (59.4%), *E. canis* 28-kDa protein 1 (55.6%) and 28-kDa protein 2 (partial) (53.6%), and OMP-1B (43.2%). The phylogenetic relationships based on amino acid sequences show that ECa28-1 and *C. ruminantium* MAP-1, *E. chaffeensis* OMP-1 proteins, and *E. canis* 28-kDa proteins 1 and 2 (partial) are related (FIG. 4).

EXAMPLE 12

Predicted Surface Probability and Immunoreactivity

Figure 6:
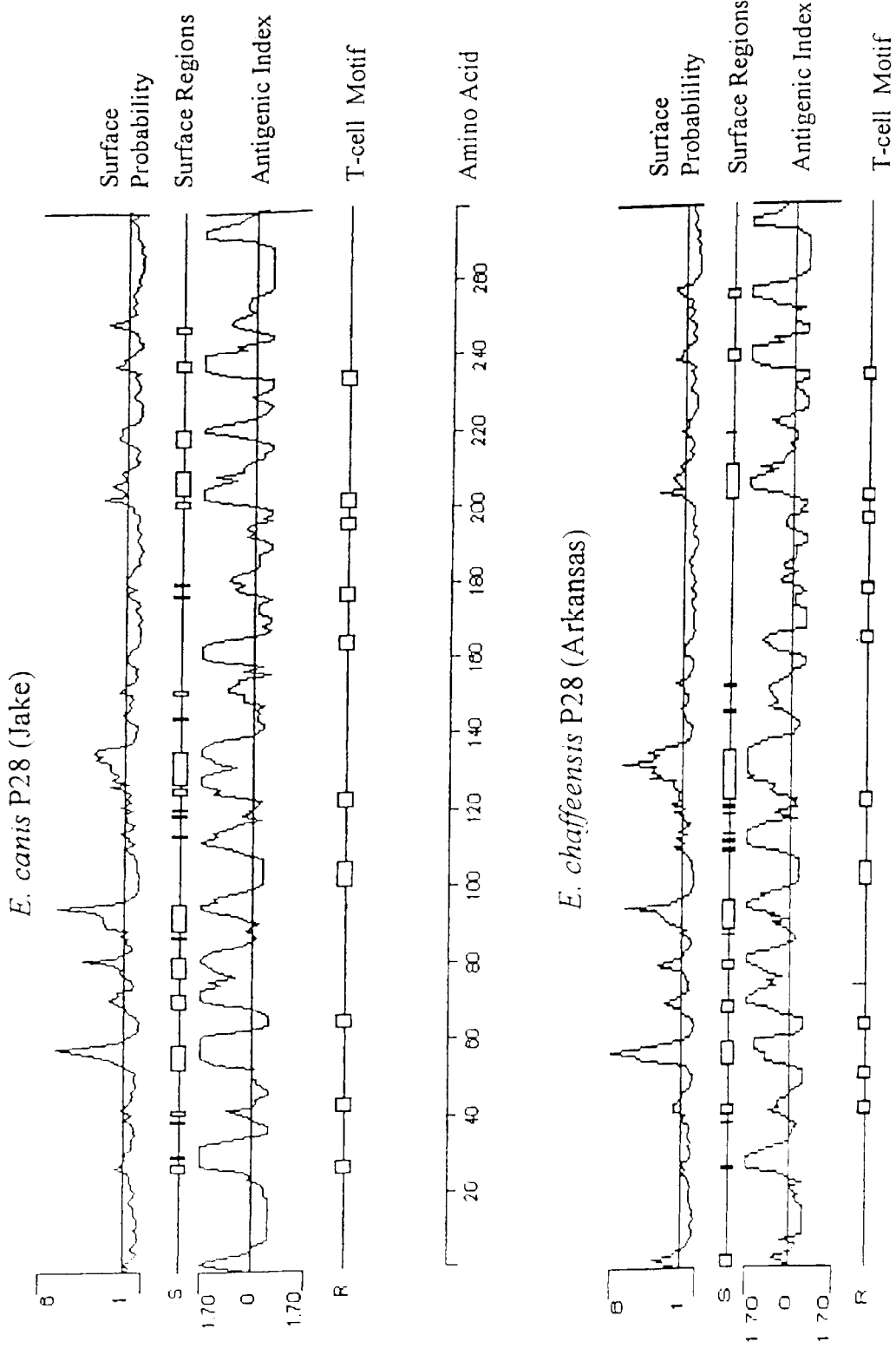
FIG. 6 shows comparison of predicted protein characteristics of ECa28-1 (Jake strain) and *E. chaffeensis* P28 (Arkansas strain). Surface probability predicts the surface residues by using a window of hexapeptide. A surface residue is any residue with a >2.0 nm$^2$ of water accessible surface area. A hexapeptide with a value higher than 1 was considered as surface region. The antigenic index predicts potential antigenic determinants. The regions with a value above zero are potential antigenic determinants. T-cell motif locates the potential T-cell antigenic determinants by using a motif of 5 amino acids with residue 1-glycine or polar, residue 2-hydrophobic, residue 3-hydrophobic, residue 4-hydrophobic or proline, and residue 5-polar or glycine. The scale indicates amino acid positions.

Analysis of *E. canis* ECa28-1 using hydropathy and hydrophilicity profiles predicted surface-exposed regions on ECa28-1 (FIG. 6). Eight major surface-exposed regions consisting of 3 to 9 amino acids were identified on ECa28-1 and were similar to the profile of surface-exposed regions on *E. chaffeensis* P28 (FIG. 6). Five of the larger surface-exposed regions on ECa28-1 were located in the N-terminal region of the protein. Surface-exposed hydrophilic regions were found in all four of the variable regions of ECa28-1. Ten T-cell motifs were predicted in the ECa28-1 using the Rothbard-Taylor aligorithm (Rothbard and Taylor, 1988), and high antigenicity of the ECa28-1 was predicted by the Jameson-Wolf antigenicity aligorithm (FIG. 6) (Jameson and Wolf, 1988). Similarities in antigenicity and T-cell motifs were observed between ECa28-1 and *E. chaffeensis* P28.

EXAMPLE 13

Detection of Homologous Genomic Copies of ECa28-1 Gene

Figure 5:
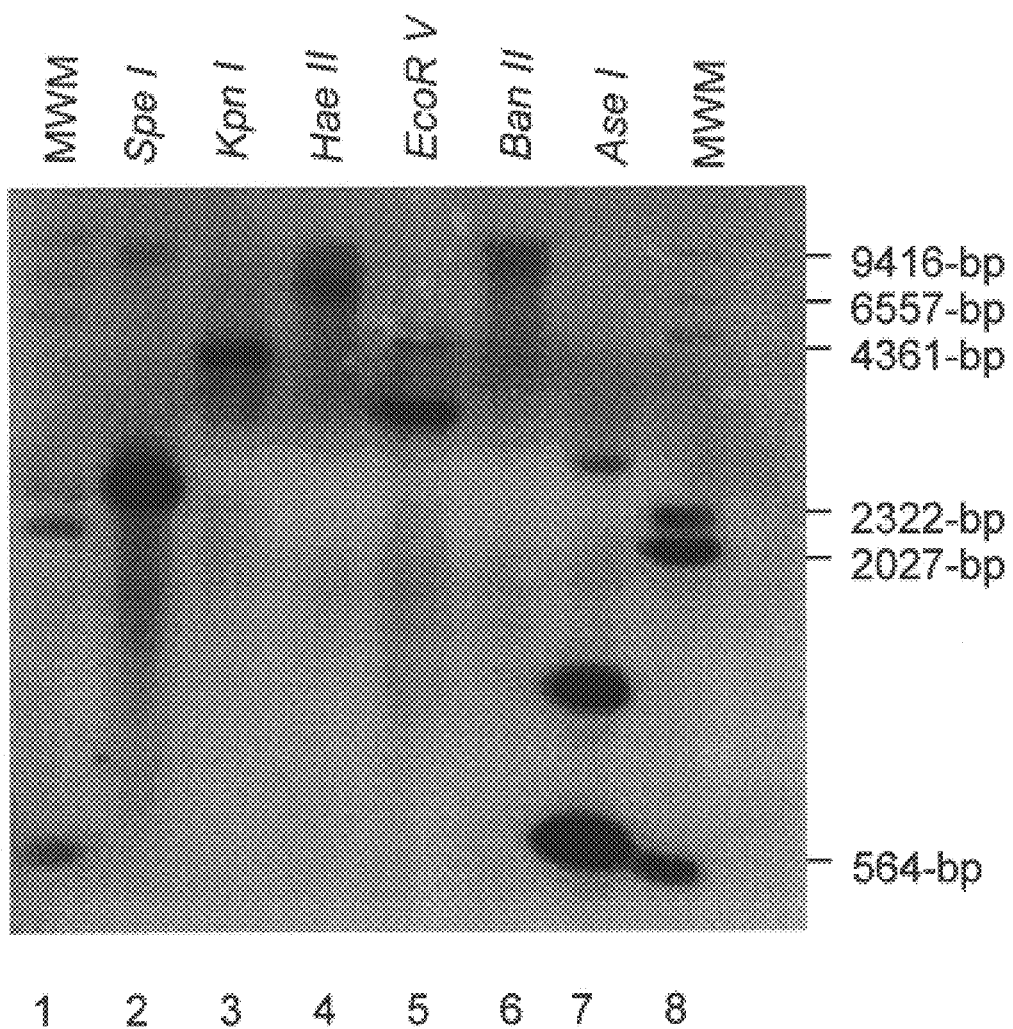
FIG. 5 shows Southern blot analysis of *E. canis* genomic DNA completely digested with six individual restriction enzymes and hybridized with a ECa28-1 DIG-labeled probe (Lanes 2–7); DIG-labeled molecular weight markers (Lanes 1 and 8).

Genomic Southern blot analysis of *E. canis* DNA completely digested independently with restriction enzymes BanII, EcoRV, HaeII, KpnI, SpeI, which do not have restriction endonuclease sites in the ECa28-1 gene, and AseI, which has internal restriction endonuclease sites at nucleotides 34, 43 and 656, revealed the presence of at least three homologous ECa28-1 gene copies (FIG. 5). Although ECa28-1 has internal Ase I internal restriction sites, the DIG-labeled probe used in the hybridization experiment targeted a region of the gene within a single DNA fragment generated by the AseI digestion of the gene. Digestion with AseI produced 3 bands (approximately 566-bp, 850-bp, and 3-kb) that hybridized with the ECa28-1 DNA probe indicating the presence of multiple genes homologous to ECa28-1 in the genome. Digestion with EcoRV and SpeI produced two bands that hybridized with the ECa28-1 gene probe.

EXAMPLE 14

Identification of 28-kDa Protein Gene Locus

Specific primers designated ECaSA3-2 (5'-CTAGGATTA GGTTATAGTATAAGTT-3', SEQ ID No. 26) corresponding to regions within ECa28SA3 and primer 793C (SEQ ID No. 23) which anneals to a region with ECa28-1 were used to amplify the intergenic region between gene SA3 and ECa28-1. The 800-bp product was sequenced with the same primers. DNA was amplified with a thermal cycling profile of 95° C. for 2 min, and 30 cycles of 95° C. for 30 sec, 50° C. for 1 min, 72° C. for 1 min followed by a 72° C. extension for 10 min and 4° C. hold.

EXAMPLE 15

Figure 8:
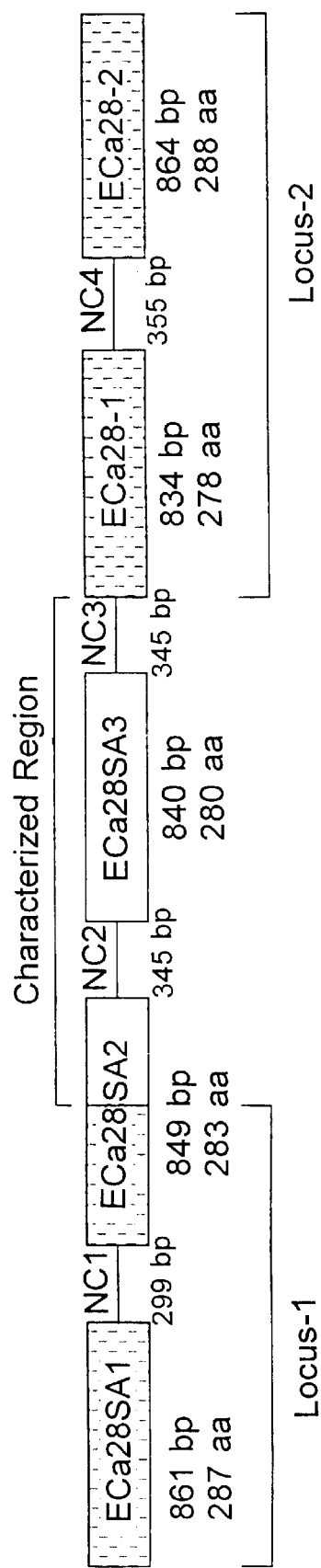
FIG. 8 shows schematic of the five *E. canis* 28-kDa protein gene locus (5.592-Kb) indicating genomic orientation and intergenic noncoding regions (28NC1-4). The 28-kDa protein genes shown in Locus 1 and 2 (shaded) have been described (McBride et al., 1999; Reddy et al., 1998; Ohashi et al., 1998). The complete sequence of ECaSA2 and a new 28-kDa protein gene designated (ECa28SA3 -unshaded) was sequenced. The noncoding intergenic regions (28NC2-3) between ECaSA2, ECa28SA3 and ECa28-1 were completed joining the previously unlinked loci 1 and 2.

PCR Amplification of 28-kDa Protein Genes and Identification of the Multiple Gene Locus In order to specifically amplify possible unknown genes downstream of ECa28SA2, primer 46f specific for ECa28SA2, and primer 1330 which targets a conserved region on the 3' end of ECa28-1 gene were used for amplification. A 2-kb PCR product was amplified with these primers that contained 2 open reading frames. The first open reading frame contained the known region of gene, ECaSA2, and a previously unsequenced 3' portion of the gene. Downstream from ECaSA2 an additional non identical, but homologous 28-kDa protein gene was found, and designated ECa28SA3. The two known loci were joined by amplification with primer SA3-2 specific for the 3' end of ECa28SA3 gene was used in conjunction with a reverse primer 793C, which anneals at 5' end of ECa28-1. An 800-bp PCR product was amplified which contained the 3' end of Eca28SA3, the intergenic region between ECa28SA3 and ECa28-1 (28NC3) and the 51 end of Eca28-1, joining the previously separate loci (FIG. 8). The 849-bp open reading frame of ECa28SA2 encodes a 283 amino acid protein, and ECa28SA3 has an 840-bp open reading frame encoding a 280 amino acid protein. The intergenic noncoding region between ECa28SA3 and ECa28-1 was 345-bp in length (FIGS. 7A–7C and 8)

EXAMPLE 16

Nucleic and Amino Acid Homology

Figure 9:
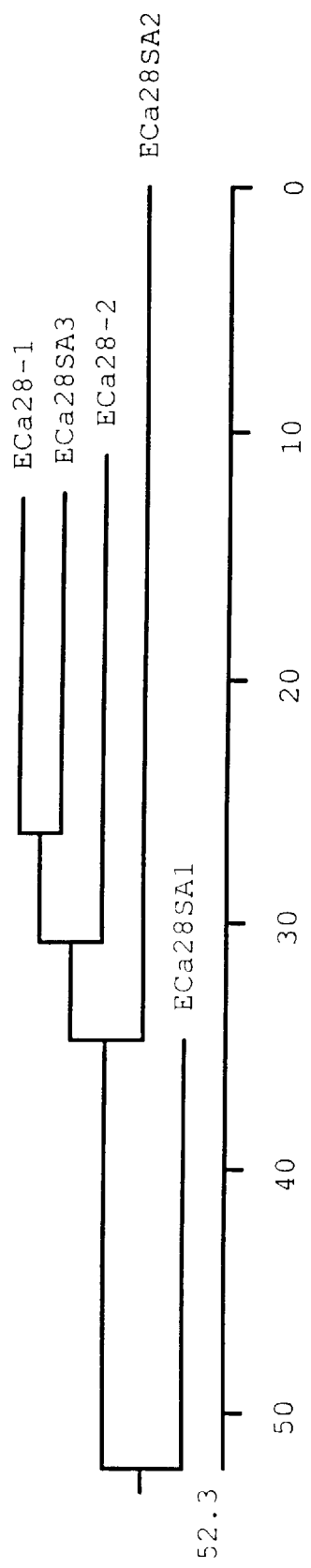
FIG. 9 shows phylogenetic relatedness of the five *E. canis* 28-kDa protein gene members based on amino acid sequences utilizing unbalanced tree construction. The length of each pair of branches represents the distance between amino acid pairs. The scale measures the distance beteween sequences.

The nucleic and amino acid sequences of all five E. canis 28-kDa protein genes were aligned using the Clustal method to examine the homology between these genes. The nucleic acid homology ranged from 58 to 75% and a similar amino acid homology of ranging from 67 to 72% was observed between the E. canis 28-kDa protein gene members (FIG. 9).

EXAMPLE 17

Transcriptional Promoter Regions

The intergenic regions between the 28-kDa protein genes were analyzed for promoter sequences by comparison with consensus *Escherichia coli* promoter regions and a promoter from *E. chaffeensis* (Yu et al., 1997; McClure, 1985).

Figure 10:
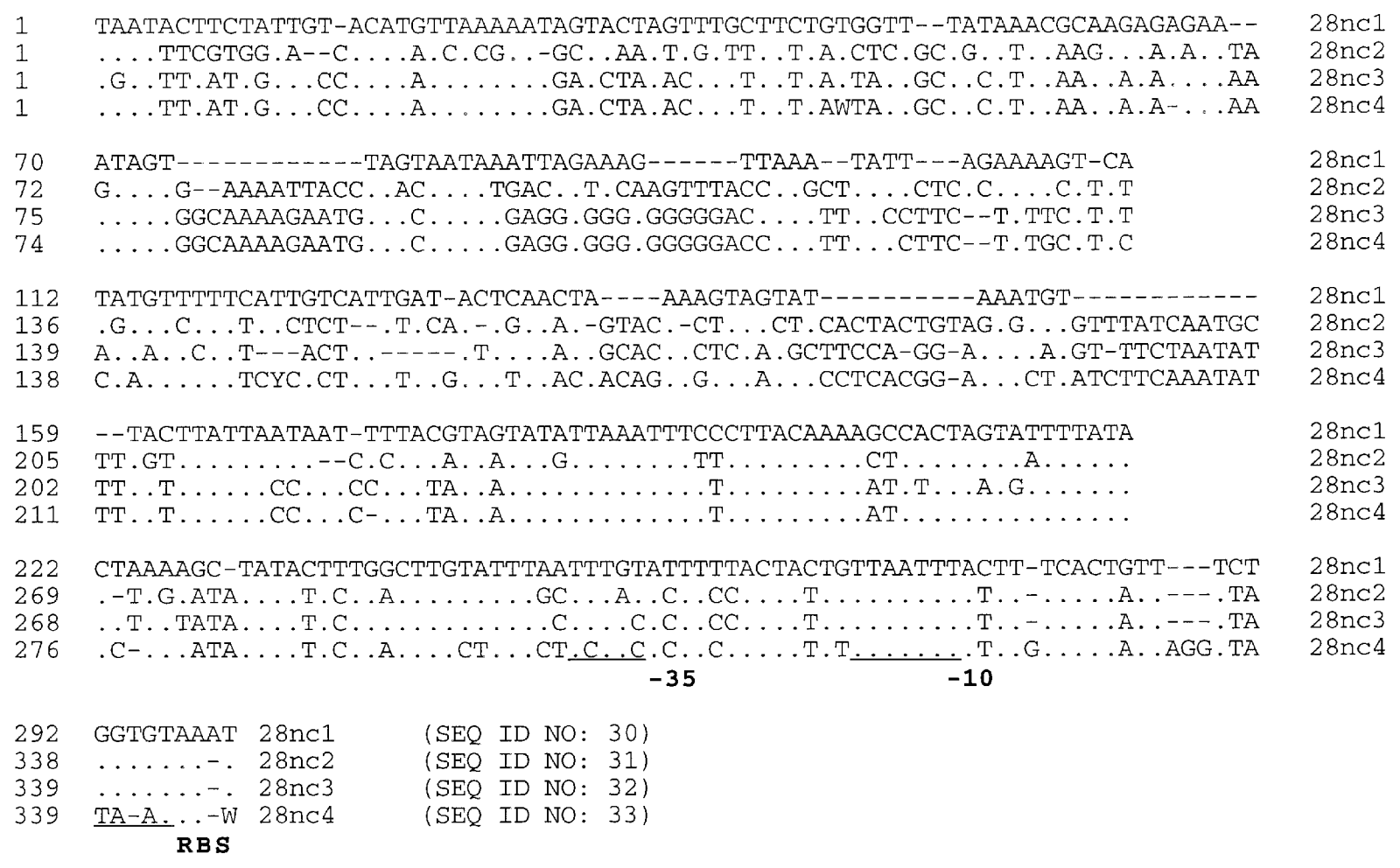

Putative promoter sequences including RBS, -10 and -35 regions were identified in 4 intergenic sequences corresponding to genes ECa28SA2, ECa28SA3, ECa28-1, and ECa28-2 (FIG. 10). The upstream noncoding region of ECa28SA1 is not known and was not analyzed.

EXAMPLE 18

N-Terminal Signal Sequence

The amino acid sequence analysis revealed that entire *E. canis* ECa28-1 has a deduced molecular mass of 30.5-kDa and the entire ECa28SA3 has a deduced molecular mass of 30.7-kDa. Both proteins have a predicted N-terminal signal peptide of 23 amino acids (MNCKKILITTALMSLMYYAPSIS, SEQ ID No. 27), which is similar to that predicted for *E. chaffeensis* P28 (MNYKKILITSALISLISSLPGV SFS, SEQ ID NO. 28), and the OMP-1 protein family (Yu et al., 1998; Ohashi et al., 1998b). A preferred cleavage site for signal peptidases (SIS; Ser-X-Ser) (Oliver, 1985) is found at amino acids 21, 22, and 23 of ECa28-1. An additional putative cleavage site at amino acid position 25 (MNCKKILITTALISLMYSIPSISSFS, SEQ ID NO. 29) identical to the predicted cleavage site of *E. chaffeensis* P28 (SFS) was also present, and would result in a mature ECa28-1 with a predicted molecular mass of 27.7-kDa. Signal cleavage site of the previously reported partial sequence of ECa28SA2 is predicted at amino acid 30. However, signal sequence analysis predicted that ECa28SA1 had an uncleavable signal sequence.

SUMMARY

Proteins of similar molecular mass have been identified and cloned from multiple rickettsial agents including *E. canis, E. chaffeensis*, and *C. ruminantium* (Reddy et al., 1998; Jongejan et al., 1993; Ohashi et al., 1998). A single locus in *Ehrlichia chaffeensis* with 6 homologous p28 genes, and 2 loci in *E. canis*, each containing some homologous 28-kDa protein genes have been previously described.

The present invention demonstrated the cloning, expression and characterization of genes encoding a mature 28-kDa protein of *E. canis* that are homologous to the omp-i multiple gene family of *E. chaffeensis* and the *C. ruminantium* map-1 gene. Two new 28-kDa protein genes were identidfied, Eca28-1 and ECa28SA3. Another *E. canis* 28-kDa protein gene, ECa28SA2, partially sequenced previously (Reddy et al., 1998), was sequenced completely in the present invention Also disclosed is the identification and characterization of a single locus in *E. canis* containing all five *E. canis* 28-kDa protein genes.

The *E. canis* 28-kDa protein are homologous to *E. chaffeensis* OMP-1 family and the MAP-1 protein of *C. rumanintium*. The most homologous *E. canis* 28-kDa proteins (ECa28SA3, ECa28-1 and ECa28-2) are sequentially arranged in the locus. Homology of these proteins ranged from 67.5% to 72.3%. Divergence among these 28-kDa proteins was 27.3% to 38.6%. *E. canis* 28-kDa proteins ECa28SA1 and ECa28SA2 were the least homologous with homology ranging from 50.9% to 59.4% and divergence of 53.3 to 69.9%. Differences between the genes lies primarily in the four hypervariable regions and suggests that these regions are surface exposed and subject to selective pressure by the immune system. Conservation of ECa28-1 among seven *E. canis* isolates has been reported (McBride et al., 1999), suggesting that *E. canis* may be clonal in North America. Conversely, significant diversity of p28 among *E. chaffeensis* isolates has been reported (Yu et al., 1998).

All of the *E. canis* 28-kDa proteins appear to be post translationally processed from a 30-kD protein to a mature 28-kD protein. Recently, a signal sequence was identified on *E. chaffeensis* P28 (Yu et al., 1998), and N-terminal amino acid sequencing has verified that the protein is post-translationally processed resulting in cleavage of the signal sequence to produce a mature protein (Ohashi et al., 1998). The leader sequences of OMP-1F and OMP-1E have also been proposed as leader signal peptides (Ohashi et al., 1998). Signal sequences identified on *E. chaffeensis* OMP-1F, OMP-1E and P28 are homologous to the leader sequence of *E. canis* 28-kDa protein. Promoter sequences for the p28 genes have not been determined experimentally, but putative promoter regions were identified by comparison with consensus sequences of the RBS, -10 and -35 promoter regions of *E. coli* and other Ehrlichiae (Yu et al., 1997; McClure, 1985). Such promoter sequences would allow each gene to potentially be transcribed and translated, suggesting that these genes may be differentially expressed in the host. Persistence of infection in dogs may be related to differential expression of p28 genes resulting in antigenic changes in vivo, thus allowing the organism to evade the immune response.

The *E. canis* 28-kda protein genes were found to exhibit nucleic acid and amino acid sequence homology with the *E. chaffeensis* omp-1 gene family and *C. ruminantium* map-1 gene. Previous studies have identified a 30-kDa protein of *E. canis* that reacts with convalescent phase antisera against *E. chaffeensis*, but was believed to be antigenically distinct (Rikihisa et al., 1994). Findings based on comparison of amino acid substitutions in four variable regions of *E. canis* 28-kDa proteins support this possibility. Together these findings also suggest that the amino acids responsible for the antigenic differences between *E. canis* and *E. chaffeensis* P28 are located in these variable regions and are readily accessible to the immune system. It was reported that immunoreactive peptides were located in the variable regions of the 28-kDa proteins of *C. ruminantium*, *E. chaffeensis* and *E. canis* (Reddy et al., 1998). Analysis of *E. canis* and *E. chaffeensis* P28 revealed that all of the variable regions have predicted surface-exposed amino acids. A study in dogs demonstrated lack of cross protection between *E. canis* and *E. chaffeensis* (Dawson and Ewing, 1992). This observation may be related to antigenic differences in the variable regions of P28 as well as in other immunologically important antigens of these ehrlichial species. Another study found that convalescent phase human antisera from *E. chaffeensis*-infected patients recognized 29/28-kDa protein (s) of *E. chaffeensis* and also reacted with homologous proteins of *E. canis* (Chen et al., 1997). Homologous and crossreactive epitopes on the *E. canis* 28-kDa protein and *E. chaffeensis* P28 appear to be recognized by the immune system.

*E. canis* 28-kDa proteins may be important immunoprotective antigens. Several reports have demonstrated that the 30-kDa antigen of *E. canis* exhibits strong immunoreactivity (Rikihisa et al., 1994; Rikihisa et al., 1992). Antibodies in convalescent phase antisera from humans and dogs have consistently reacted with proteins in this size range from *E. chaffeensis* and *E. canis,* suggesting that they may be important immunoprotective antigens (Rikihisa et al., 1994; Chen et al., 1994; Chen et al., 1997). In addition, antibodies to 30, 24 and 21-kDa proteins developed early in the immune response to *E. canis* (Rikihisa et al., 1994; Rikihisa et al., 1992), suggesting that these proteins may be especially important in the immune responses in the acute stage of disease. Recently, a family of homologous genes encoding outer membrane proteins with molecular masses of 28-kDa have been identified in *E. chaffeensis,* and mice immunized with recombinant *E. chaffeensis* P28 appeared to have developed immunity against homologous challenge (Ohashi et al., 1998). The P28 of *E. chaffeensis* has been demonstrated to be present in the outer membrane, and immuno-electron microscopy has localized the P28 on the surface on the organism, and thus suggesting that it may serve as an adhesin (Ohashi et al., 1998). It is likely that the 28-kDa proteins of *E. canis* identified in this study have the same location and possibly serve a similar function.

Comparison of ECa28-1 from different strains of *E. canis* revealed that the gene is apparently completely conserved. Studies involving *E. chaffeensis* have demonstrated immunologic and molecular evidence of diversity in the ECa28-1. Patients infected with *E. chaffeensis* have variable immunoreactivity to the 29/28-kDa proteins, suggesting that there is antigenic diversity (Chen et al., 1997). Recently molecular evidence has been generated to support antigenic diversity in the p28 gene from *E. chaffeensis* (Yu et al., 1998). A comparison of five *E. chaffeensis* isolates revealed that two isolates (Sapulpa and St. Vincent) were 100% identical, but three others (Arkansas, Jax, 91HE17) were divergent by as much as 13.4% at the amino acid level. The conservation of ECa28-1 suggests that *E. canis* strains found in the United States may be genetically identical, and thus *E. canis* 28-kDa protein is an attractive vaccine candidate for canine ehrlichiosis in the United States. Further analysis of *E. canis* isolates outside the United States may provide information regarding the origin and evolution of *E. canis.* Conservation of the 28-kDa protein makes it an important potential candidate for reliable serodiagnosis of canine ehrlichiosis.

The role of multiple homologous genes is not known at this point; however, persistence of *E. canis* infections in dogs could conceivably be related to antigenic variation due to variable expression of homologous 28-kDa protein genes, thus enabling *E. canis* to evade immune surveillance. Variation of msp-3 genes in *A. marginale* is partially responsible for variation in the MSP-3 protein, resulting in persistent infections (Alleman et al., 1997). Studies to examine 28-kDa protein gene expression by *E. canis* in acutely and chronically infected dogs would provide insight into the role of the 28-kDa protein gene family in persistence of infection.

The following references were cited herein.
Alleman A. R., et al., (1997) *Infect Immun* 65: 156–163.
Anderson B. E., et al., (1991) *J Clin Microbiol* 29: 2838–2842.
Anderson B. E., et al., (1992) *Int J Syst Bacteriol* 42: 299–302.
Brouqui P., et al., (1992) *J Clin Microbiol* 30: 1062–1066.
Chen S. M., et al., (1997) *Clin Diag Lab Immunol* 4: 731–735.
Chen S. M., et al., (1994) *Am J Trop Med Hyg* 50: 52–58.
Dawson J. E., et al., (1992) *Am J Vet Res* 53: 1322–1327.
Dawson J. E., et al., (1991) *J Infect Dis* 163: 564–567.
Donatien, et al., (1935) *Bull Soc Pathol Exot* 28: 418–9.
Ewing, (1963) *J Am Vet Med Assoc* 143: 503–6.
Groves M. G., et al., (1975) *Am J Vet Res* 36: 937–940.

Harrus S., et al., (1998) *J Clin Microbiol* 36: 73–76.
Jameson B. A., et al., (1988) *CABIOS* 4: 181–186.
Jongejan F., et al., (1993) *Rev Elev Med Vet Pays Trop* 46: 145–152.
McBride J. W., et al., (1996) *J Vet Diag Invest* 8: 441–447.
McBride, et al., (1999) *Clin Diagn Lab Immunol.; (In press)*.
McClure, (1985) *Ann Rev Biochem* 54: 171–204.
McGeoch D. J. (1985) *Virus Res* 3: 271–286.
Nyindo M., et al., (1991) *Am J Vet Res* 52: 1225–1230.
Nyindo, et al., (1971) *Am J Vet Res* 32: 1651–58.
Ohashi, et al., (1998) *Infect Immun* 66: 132–9.
Ohashi, et al., (1998) *J Clin Microb* 36: 2671–80
Reddy, et al., (1998) *Biochem Biophys Res Comm* 247: 636–43.
Rikihisa, et al., (1994) *J Clin Microbiol* 32: 2107–12.
Rothbard J. B., et al., (1988) *The EMBO J7*: 93–100.
Sambrook J., et al., (1989) In *Molecular Cloning: A Laboratory Manual*. Cold Spring Harbor: Cold Spring Harbor Press.
Troy G. C., et al., (1990) Canine ehrlichiosis. In *Infectious diseases of the dog and cat*. Green C. E. (ed). Philidelphia: W. B. Sauders Co.
von Heijne, (1986) *Nucl Acids Res* 14: 4683–90.
Walker, et al., (1970) *J Am Vet Med Assoc* 157: 43–55.
Weiss E., et al., (1975) *Appl Microbiol* 30: 456–463.
Yu, et al., (1997) *Gene* 184: 149–154.
Yu, et al., (1998) *J. Clin. Microbiol. (In press)*.

Any patents or publications mentioned in this specification are indicative of the levels of those skilled in the art to which the invention pertains. These patents and publications are herein incorporated by reference to the same extent as if each individual publication was individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA sequences encoding a 30-kilodalton protein of *Ehrlichia canis*, wherein said protein is immunoreactive with anti-*Ehrlichia canis* serum.

2. The isolated DNA sequences of claim 1, wherein said protein has an amino acid sequence selected from the group consisting of SEQ ID No. 4 and SEQ ID No. 6.

3. The isolated DNA sequences of claim 2, wherein said protein has an N-terminal signal sequence.

4. The isolated DNA sequences of claim 3, wherein said protein is post-translationally modified to a 28-kilodalton protein.

5. The isolated DNA sequences of claim 1, wherein said DNA has a sequence selected from the group consisting of SEQ ID No. 1, SEQ ID No. 3 and SEQ ID No. 5.

6. The isolated DNA sequences of claim 1, wherein said DNA is contained in a single locus of *Ehrlichia canis*.

7. The isolated DNA sequences of claim 6, wherein said locus is a multigene locus of 5.592 kb in length.

8. The isolated DNA sequences of claim 7, wherein said locus encoding homologous post-translationally modified 28-kilodalton proteins of *Ehrlichia canis*.

9. The isolated DNA sequences of claim 8, wherein said homologous post-translationally modified 28-kilodalton proteins of *Ehrlichia canis* are selected from the group consisting of ECa28SA1, ECa28SA2, ECa28SA3, ECa28-1 and ECa28-2.

10. A vector comprising the DNA sequences of claim 1.

11. The vector of claim 10, wherein said vector is an expression vector capable of expressing a peptide or polypeptide encoded by the sequence selected from the group consisting of SEQ ID No. 1, SEQ ID No. 3 and SEQ ID No. 5 when said expression vector is introduced into a cell.

12. A host cell containing the isolated DNA sequences of claim 5.

* * * * *

UNITED STATES PATENT AND TRADEMARK OFFICE
CERTIFICATE OF CORRECTION

PATENT NO.    : 6,403,780 B1
DATED         : June 11, 2002
INVENTOR(S)   : David H. Walker, Xue-Jie Yu and Jere W. McBride It is certified that error appears in the above-identified patent and that said Letters Patent is hereby corrected as shown below:

Column 7,
Line 52, please insert the word -- of -- between "use" and "the".

Column 10,
Line 45, please delete the words "for a".

Column 13,
Line 19, "precludes" should read -- preclude --.

Column 14,
Line 34, "aligorithm" should read -- algorithm --.

Column 16,
Line 45, "hr" should read -- hrs --.
Line 48, "a" should read -- an --.

Column 17,
Line 21, "aligorithm" should read -- algorithm --.
Line 45, "31" should read -- 3' --.

Column 19,
Line 46, please insert the word -- which -- before "was used".
Line 51, "51" should read -- 5' --.

Column 20,
Line 60, please insert the word -- genes -- before "are homolgous".

Column 23,
Line 21, "Philidelphia" should read -- Philadelphia --.

UNITED STATES PATENT AND TRADEMARK OFFICE
CERTIFICATE OF CORRECTION

PATENT NO.   : 6,403,780 B1
DATED        : June 11, 2002
INVENTOR(S)  : David H. Walker, Xue-Jie Yu and Jere W. McBride It is certified that error appears in the above-identified patent and that said Letters Patent is hereby corrected as shown below:

<u>Column 53,</u>
Lines 62 and 65, "sequences" should read -- sequence --.

Signed and Sealed this

Eighteenth Day of March, 2003

JAMES E. ROGAN
*Director of the United States Patent and Trademark Office*

SEQUENCE LISTING

<160> NUMBER OF SEQ ID NOS: 33

<210> SEQ ID NO 1
<211> LENGTH: 1607
<212> TYPE: DNA
<213> ORGANISM: Ehrlichia canis
<220> FEATURE:
<223> OTHER INFORMATION: nucleic acid sequence of ECa28-1

<400> SEQUENCE: 1

```
attttattta ttaccaatct tatataatat attaaatttc tcttacaaaa atctctaatg      60
ttttataccT aatatatata ttctggcttg tatctacttt gcacttccac tattgttaat     120
ttattttcac tattttaggt gtaatatgaa ttgcaaaaaa attcttataa caactgcatt     180
aatatcatta atgtactcta ttccaagcat atcttttcT gatactatac aagatggtaa     240
catgggtggt aacttctata ttagtggaaa gtatgtacca agtgtctcac attttggtag     300
cttctcagct aaagaagaaa gcaaatcaac tgttggagtt tttggattaa aacatgattg     360
ggatggaagt ccaatactta agaataaaca cgctgacttt actgttccaa actattcgtt     420
cagatacgag aacaatccat ttctagggtt tgcaggagct atcggttact caatgggtgg     480
cccaagaata gaattcgaaa tatcttatga agcattcgac gtaaaaagtc ctaatatcaa     540
ttatcaaaat gacgcgcaca ggtactgcgc tctatctcat cacacatcgg cagccatgga     600
agctgataaa tttgtcttct taaaaaacga agggttaatt gacatatcac ttgcaataaa     660
tgcatgttat gatataataa atgacaaagt acctgtttct ccttatatat gcgcaggtat     720
tggtactgat ttgatttcta tgtttgaagc tacaagtcct aaaatttcct accaaggaaa     780
actgggcatt agttactcta ttaatccgga aacctctgtt ttcatcggtg ggcatttcca     840
caggatcata ggtaatgagt ttagagatat tcctgcaata gtacctagta actcaactac     900
aataagtgga ccacaatttg caacagtaac actaaatgtg tgtcactttg gtttagaact     960
tggaggaaga tttaacttct aattttattg ttgccacata ttaaaaatga tctaaacttg    1020
tttttawtat tgctacatac aaaaaagaa aaatagtggc aaaagaatgt agcaataaga    1080
```

-continued

```
gggggggggg ggaccaaatt tatcttctat gcttcccaag ttttttcycg ctatttatga    1140
cttaaacaac agaaggtaat atcctcacgg aaaacttatc ttcaaatatt ttatttatta    1200
ccaatcttat ataatatatt aaatttctct tacaaaaatc actagtattt ataccaaaa     1260 tatatattct gacttgcttt tcttctgcac ttctactatt tttaatttat ttgtcactat    1320
taggttataa taawatgaat tgcmaaagat ttttcatagc aagtgcattg atatcactaa    1380
tgtctttctt acctagcgta tcttttttctg aatcaataca tgaagataat ataaatggta   1440
acttttacat tagtgcaaag tatatgccaa gtgcctcaca ctttggcgta ttttcagtta   1500
aagaagagaa aaacacaaca actggagttt tcggattaaa acaagattgg gacggagcaa   1560
cactaaagga tgcaagcwgc agccacacaw tagacccaag tacaatg                 1607
```

<210> SEQ ID NO 2
<211> LENGTH: 278
<212> TYPE: PRT
<213> ORGANISM: Ehrlichia canis
<220> FEATURE:
<223> OTHER INFORMATION: amino acid sequence of ECa28-1 protein

<400> SEQUENCE: 2

```
Met Asn Cys Lys Lys Ile Leu Ile Thr Thr Ala Leu Ile Ser Leu
                5                  10                  15

Met Tyr Ser Ile Pro Ser Ile Ser Phe Ser Asp Thr Ile Gln Asp
               20                  25                  30

Gly Asn Met Gly Gly Asn Phe Tyr Ile Ser Gly Lys Tyr Val Pro
               35                  40                  45

Ser Val Ser His Phe Gly Ser Phe Ser Ala Lys Glu Glu Ser Lys
               50                  55                  60

Ser Thr Val Gly Val Phe Gly Leu Lys His Asp trp Asp Gly Ser
               65                  70                  75

Pro Ile Leu Lys Asn Lys His Ala Asp Phe Thr Val Pro Asn Tyr
               80                  85                  90

Ser Phe Arg Tyr Glu Asn Asn Pro Phe Leu Gly Phe Ala Gly Ala
               95                 100                 105

Ile Gly Tyr Ser Met Gly Gly Pro Arg Ile Glu Phe Glu Ile Ser
              110                 115                 120

Tyr Glu Ala Phe Asp Val Lys Ser Pro Asn Ile Asn Tyr Gln Asn
              125                 130                 135

Asp Ala His Arg Tyr Cys Ala Leu Ser His His Thr Ser Ala Ala
              140                 145                 150

Met Glu Ala Asp Lys Phe Val Phe Leu Lys Asn Glu Gly Leu Ile
              155                 160                 165

Asp Ile Ser Leu Ala Ile Asn Ala Cys Tyr Asp Ile Ile Asn Asp
              170                 175                 180

Lys Val Pro Val Ser Pro Tyr Ile Cys Ala Gly Ile Gly Thr Asp
              185                 190                 195

Leu Ile Ser Met Phe Glu Ala Thr Ser Pro Lys Ile Ser Tyr Gln
              200                 205                 210

Gly Lys Leu Gly Ile Ser Tyr Ser Ile Asn Pro Glu Thr Ser Val
              215                 220                 225

Phe Ile Gly Gly His Phe His Arg Ile Ile Gly Asn Glu Phe Arg
              230                 235                 240

Asp Ile Pro Ala Ile Val Pro Ser Asn Ser Thr Thr Ile Ser Gly
              245                 250                 255
```

-continued

```
Pro Gln Phe Ala Thr Val Thr Leu Asn Val Cys His Phe Gly Leu
            260                 265                 270

Glu Leu Gly Gly Arg Phe Asn Phe
            275

<210> SEQ ID NO 3
<211> LENGTH: 849
<212> TYPE: DNA
<213> ORGANISM: Ehrlichia canis
<220> FEATURE:
<221> NAME/KEY: mat_peptide
<223> OTHER INFORMATION: nucleic acid sequence of ECa28SA2

<400> SEQUENCE: 3
atgaattgta aaaagtttt cacaataagt gcattgatat catccatata cttcctacct      60
aatgtctcat actctaaccc agtatatggt aacagtatgt atggtaattt ttacatatca    120
ggaaagtaca tgccaagtgt tcctcatttt ggatttttt cagctgaaga agagaaaaaa    180
aagacaactg tagtatatgg cttaaaagaa actgggcag gagatgcaat atctagtcaa    240
agtccagatg ataattttac cattcgaaat tactcattca gtatgcaag caacaagttt    300 ttagggtttg cagtagctat tggttactcg ataggcagtc caagaataga agttgagatg    360
tcttatgaag catttgatgt gaaaaatcca ggtgataatt acaaaaacgg tgcttacagg    420
tattgtgctt tatctcatca agatgatgcg gatgatgaca tgactagtgc aactgacaaa    480
tttgtatatt taattaatga aggattactt aacatatcat ttatgacaaa catatgttat    540
gaaacagcaa gcaaaaatat acctctctct ccttacatat gtgcaggtat tggtactgat    600
ttaattcaca tgtttgaaac tacacatcct aaaatttctt atcaaggaaa gctagggttg    660
gcctacttcg taagtgcaga gtcttcggtt tcttttggta tatattttca taaaattata    720
aataataagt ttaaaaatgt tccagccatg gtacctatta actcagacga gatagtagga    780
ccacagtttg caacagtaac attaaatgta tgctactttg gattagaact tggatgtagg    840
ttcaacttc                                                             849

<210> SEQ ID NO 4
<211> LENGTH: 283
<212> TYPE: PRT
<213> ORGANISM: Ehrlichia canis
<220> FEATURE:
<223> OTHER INFORMATION: amino acid sequence of ECa28SA2 protein

<400> SEQUENCE: 4

Met Asn Cys Lys Lys Val Phe Thr Ile Ser Ala Leu Ile Ser Ser
              5                  10                  15

Ile Tyr Phe Leu Pro Asn Val Ser Tyr Ser Asn Pro Val Tyr Gly
             20                  25                  30

Asn Ser Met Tyr Gly Asn Phe Tyr Ile Ser Gly Lys Tyr Met Pro
             35                  40                  45

Ser Val Pro His Phe Gly Ile Phe Ser Ala Glu Glu Lys Lys
             50                  55                  60

Lys Thr Thr Val Val Tyr Gly Leu Lys Glu Asn Trp Ala Gly Asp
             65                  70                  75

Ala Ile Ser Ser Gln Ser Pro Asp Asp Asn Phe Thr Ile Arg Asn
             80                  85                  90

Tyr Ser Phe Lys Tyr Ala Ser Asn Lys Phe Leu Gly Phe Ala Val
             95                 100                 105

Ala Ile Gly Tyr Ser Ile Gly Ser Pro Arg Ile Glu Val Glu Met
```

```
                110                 115                 120
Ser Tyr Glu Ala Phe Asp Val Lys Asn Pro Gly Asp Asn Tyr Lys
                125                 130                 135
Asn Gly Ala Tyr Arg Tyr Cys Ala Leu Ser His Gln Asp Asp Ala
                140                 145                 150
Asp Asp Asp Met Thr Ser Ala Thr Asp Lys Phe Val Tyr Leu Ile
                155                 160                 165
Asn Glu Gly Leu Leu Asn Ile Ser Phe Met Thr Asn Ile Cys Tyr
                170                 175                 180
Glu Thr Ala Ser Lys Asn Ile Pro Leu Ser Pro Tyr Ile Cys Ala
                185                 190                 195
Gly Ile Gly Thr Asp Leu Ile His Met Phe Glu Thr Thr His Pro
                200                 205                 210
Lys Ile Ser Tyr Gln Gly Lys Leu Gly Leu Ala Tyr Phe Val Ser
                215                 220                 225
Ala Glu Ser Ser Val Ser Phe Gly Ile Tyr Phe His Lys Ile Ile
                230                 235                 240
Asn Asn Lys Phe Lys Asn Val Pro Ala Met Val Pro Ile Asn Ser
                245                 250                 255
Asp Glu Ile Val Gly Pro Gln Phe Ala Thr Val Thr Leu Asn Val
                260                 265                 270
Cys Tyr Phe Gly Leu Glu Leu Gly Cys Arg Phe Asn Phe
                275                 280

<210> SEQ ID NO 5
<211> LENGTH: 840
<212> TYPE: DNA
<213> ORGANISM: Ehrlichia canis
<220> FEATURE:
<221> NAME/KEY: mat_peptide
<223> OTHER INFORMATION: nucleic acid sequence of ECa28SA3

<400> SEQUENCE: 5
atgaattgca aaaaattct tataacaact gcattaatgt cattaatgta ctatgctcca      60
agcatatctt tttctgatac tatacaagac gataacactg gtagcttcta catcagtgga    120
aaatatgtac caagtgtttc acattttggt gttttctcag ctaaagaaga agaaaactca    180
actgttggag tttttggatt aaaacatgat tggaatggag gtacaatatc taactcttct    240
ccagaaaata tattcacagt tcaaaattat tcgtttaaat acgaaaacaa cccattctta    300
gggtttgcag gagctattgg ttattcaatg ggtggcccaa gaatagaact tgaagttctg    360
tacgagacat tcgatgtgaa aaatcagaac aataattata agaacggcgc acacagatac    420
tgtgctttat ctcatcatag ttcagcaaca agcatgtcct ccgcaagtaa caaatttgtt    480
ttcttaaaaa atgaagggtt aattgactta tcatttatga taaatgcatg ctatgacata    540
ataattgaag gaatgccttt tcacccttat atttgtgcag gtgttggtac tgatgttgtt    600
tccatgtttg aagctataaa tcctaaaatt tcttaccaag gaaaactagg attaggttat    660
agtataagtt cagaagcctc tgtttttatc ggtggacact tcacagagt catagggtaat    720 gaatttagag acatccctgc tatggttcct agtggatcaa atcttccaga aaaccaattt    780
gcaatagtaa cactaaatgt gtgtcacttt ggcatagaac ttggaggaag atttaacttc    840

<210> SEQ ID NO 6
<211> LENGTH: 280
<212> TYPE: PRT
<213> ORGANISM: Ehrlichia canis
```

```
<220> FEATURE:
<223> OTHER INFORMATION: amino acid sequence of ECa28SA3 protein

<400> SEQUENCE: 6

Met Asn Cys Lys Lys Ile Leu Ile Thr Thr Ala Leu Met Ser Leu
                  5                  10                  15

Met Tyr Tyr Ala Pro Ser Ile Ser Phe Ser Asp Thr Ile Gln Asp
                 20                  25                  30

Asp Asn Thr Gly Ser Phe Tyr Ile Ser Gly Lys Tyr Val Pro Ser
                 35                  40                  45

Val Ser His Phe Gly Val Phe Ser Ala Lys Glu Glu Arg Asn Ser
                 50                  55                  60

Thr Val Gly Val Phe Gly Leu Lys His Asp Trp Asn Gly Gly Thr
                 65                  70                  75

Ile Ser Asn Ser Ser Pro Glu Asn Ile Phe Thr Val Gln Asn Tyr
                 80                  85                  90

Ser Phe Lys Tyr Glu Asn Asn Pro Phe Leu Gly Phe Ala Gly Ala
                 95                 100                 105

Ile Gly Tyr Ser Met Gly Gly Pro Arg Ile Glu Leu Glu Val Leu
                110                 115                 120

Tyr Glu Thr Phe Asp Val Lys Asn Gln Asn Asn Asn Tyr Lys Asn
                125                 130                 135

Gly Ala His Arg Tyr Cys Ala Leu Ser His His Ser Ser Ala Thr
                140                 145                 150

Ser Met Ser Ser Ala Ser Asn Lys Phe Val Phe Leu Lys Asn Glu
                155                 160                 165

Gly Leu Ile Asp Leu Ser Phe Met Ile Asn Ala Cys Tyr Asp Ile
                170                 175                 180

Ile Ile Glu Gly Met Pro Phe Ser Pro Tyr Ile Cys Ala Gly Val
                185                 190                 195

Gly Thr Asp Val Val Ser Met Phe Glu Ala Ile Asn Pro Lys Ile
                200                 205                 210

Ser Tyr Gln Gly Lys Leu Gly Leu Gly Tyr Ser Ile Ser Ser Glu
                215                 220                 225

Ala Ser Val Phe Ile Gly Gly His Phe His Arg Val Ile Gly Asn
                230                 235                 240

Glu Phe Arg Asp Ile Pro Ala Met Val Pro Ser Gly Ser Asn Leu
                245                 250                 255

Pro Glu Asn Gln Phe Ala Ile Val Thr Leu Asn Val Cys His Phe
                260                 265                 270

Gly Ile Glu Leu Gly Gly Arg Phe Asn Phe
                275                 280

<210> SEQ ID NO 7
<211> LENGTH: 133
<212> TYPE: PRT
<213> ORGANISM: Ehrlichia canis
<220> FEATURE:
<223> OTHER INFORMATION: partial amino acid sequence of ECa28SA2 protein

<400> SEQUENCE: 7

Met Asn Cys Lys Lys Val Phe Thr Ile Ser Ala Leu Ile Ser Ser
                  5                  10                  15

Ile Tyr Phe Leu Pro Asn Val Ser Tyr Ser Asn Pro Val Tyr Gly
                 20                  25                  30

Asn Ser Met Tyr Gly Asn Phe Tyr Ile Ser Gly Lys Tyr Met Pro
```

```
                       35                  40                  45
Ser Val Pro His Phe Gly Ile Phe Ser Ala Glu Glu Lys Lys
                50                  55                  60
Lys Thr Thr Val Val Tyr Gly Leu Lys Glu Asn Trp Ala Gly Asp
                65                  70                  75
Ala Ile Ser Ser Gln Ser Pro Asp Asp Asn Phe Thr Ile Arg Asn
                80                  85                  90
Tyr Ser Phe Lys Tyr Ala Ser Asn Lys Phe Leu Gly Phe Ala Val
                95                 100                 105
Ala Ile Gly Tyr Ser Ile Gly Ser Pro Arg Ile Glu Val Glu Met
               110                 115                 120
Ser Tyr Glu Ala Phe Asp Val Lys Asn Gln Gly Asn Asn
               125                 130

<210> SEQ ID NO 8
<211> LENGTH: 287
<212> TYPE: PRT
<213> ORGANISM: Ehrlichia canis
<220> FEATURE:
<223> OTHER INFORMATION: amino acid sequence of ECa28SA1 protien

<400> SEQUENCE: 8

Met Lys Tyr Lys Lys Thr Phe Thr Val Thr Ala Leu Val Leu Leu
                 5                  10                  15
Thr Ser Phe Thr His Phe Ile Pro Phe Tyr Ser Pro Ala Arg Ala
                20                  25                  30
Ser Thr Ile His Asn Phe Tyr Ile Ser Gly Lys Tyr Met Pro Thr
                35                  40                  45
Ala Ser His Phe Gly Ile Phe Ser Ala Lys Glu Glu Gln Ser Phe
                50                  55                  60
Thr Lys Val Leu Val Gly Leu Asp Gln Arg Leu Ser His Asn Ile
                65                  70                  75
Ile Asn Asn Asp Thr Ala Lys Ser Leu Lys Val Gln Asn Tyr
                80                  85                  90
Ser Phe Lys Tyr Lys Asn Asn Pro Phe Leu Gly Phe Ala Gly Ala
                95                 100                 105
Ile Gly Tyr Ser Ile Gly Asn Ser Arg Ile Glu Leu Glu Val Ser
               110                 115                 120
His Glu Ile Phe Asp Thr Lys Asn Pro Gly Asn Asn Tyr Leu Asn
               125                 130                 135
Asp Ser His Lys Tyr Cys Ala Leu Ser His Gly Ser His Ile Cys
               140                 145                 150
Ser Asp Gly Asn Ser Gly Asp Trp Tyr Thr Ala Lys Thr Asp Lys
               155                 160                 165
Phe Val Leu Leu Lys Asn Glu Gly Leu Leu Asp Val Ser Phe Met
               170                 175                 180
Leu Asn Ala Cys Tyr Asp Ile Thr Thr Glu Lys Met Pro Phe Ser
               185                 190                 195
Pro Tyr Ile Cys Ala Gly Ile Gly Thr Asp Leu Ile Ser Met Phe
               200                 205                 210
Glu Thr Thr Gln Asn Lys Ile Ser Tyr Gln Gly Lys Leu Gly Leu
               215                 220                 225
Asn Tyr Thr Ile Asn Ser Arg Val Ser Val Phe Ala Gly Gly His
               230                 235                 240
Phe His Lys Val Ile Gly Asn Glu Phe Lys Gly Ile Pro Thr Leu
```

-continued

```
                245                 250                 255

Leu Pro Asp Gly Ser Asn Ile Lys Val Gln Gln Ser Ala Thr Val
                260                 265                 270

Thr Leu Asp Val Cys His Phe Gly Leu Glu Ile Gly Ser Arg Phe
                275                 280                 285

Phe Phe

<210> SEQ ID NO 9
<211> LENGTH: 281
<212> TYPE: PRT
<213> ORGANISM: Ehrlichia chaffeensis
<220> FEATURE:
<223> OTHER INFORMATION: amino acid sequence of E. chaffeensis P28

<400> SEQUENCE: 9

Met Asn Tyr Lys Lys Val Phe Ile Thr Ser Ala Leu Ile Ser Leu
                5                   10                  15

Ile Ser Ser Leu Pro Gly Val Ser Phe Ser Asp Pro Ala Gly Ser
                20                  25                  30

Gly Ile Asn Gly Asn Phe Tyr Ile Ser Gly Lys Tyr Met Pro Ser
                35                  40                  45

Ala Ser His Phe Gly Val Phe Ser Ala Lys Glu Glu Arg Asn Thr
                50                  55                  60

Thr Val Gly Val Phe Gly Leu Lys Gln Asn Trp Asp Gly Ser Ala
                65                  70                  75

Ile Ser Asn Ser Ser Pro Asn Asp Val Phe Thr Val Ser Asn Tyr
                80                  85                  90

Ser Phe Lys Tyr Glu Asn Asn Pro Phe Leu Gly Phe Ala Gly Ala
                95                  100                 105

Ile Gly Tyr Ser Met Asp Gly Pro Arg Ile Glu Leu Glu Val Ser
                110                 115                  120

Tyr Glu Thr Phe Asp Val Lys Asn Gln Gly Asn Asn Tyr Lys Asn
                125                 130                 135

Glu Ala His Arg Tyr Cys Ala Leu Ser His Asn Ser Ala Ala Asp
                140                 145                 150

Met Ser Ser Ala Ser Asn Asn Phe Val Phe Leu Lys Asn Glu Gly
                155                 160                 165

Leu Leu Asp Ile Ser Phe Met Leu Asn Ala Cys Tyr Asp Val Val
                170                 175                 180

Gly Glu Gly Ile Pro Phe Ser Pro Tyr Ile Cys Ala Gly Ile Gly
                185                 190                 195

Thr Asp Leu Val Ser Met Phe Glu Ala Thr Asn Pro Lys Ile Ser
                200                 205                 210

Tyr Gln Gly Lys Leu Gly Leu Ser Tyr Ser Ile Ser Pro Glu Ala
                215                 220                 225

Ser Val Phe Ile Gly Gly His Phe His Lys Val Ile Gly Asn Glu
                230                 235                 240

Phe Arg Asp Ile Pro Thr Ile Ile Pro Thr Gly Ser Thr Leu Ala
                245                 250                 255

Gly Lys Gly Asn Tyr Pro Ala Ile Val Ile Leu Asp Val Cys His
                260                 265                 270

Phe Gly Ile Glu Leu Gly Gly Arg Phe Ala Phe
                275                 280

<210> SEQ ID NO 10
```

-continued

```
<211> LENGTH: 283
<212> TYPE: PRT
<213> ORGANISM: Ehrlichia chaffeensis
<220> FEATURE:
<223> OTHER INFORMATION: amino acid sequence of E. chaffeensis OMP-1B

<400> SEQUENCE: 10

Met Asn Tyr Lys Lys Ile Phe Val Ser Ser Ala Leu Ile Ser Leu
                5                   10                  15

Met Ser Ile Leu Pro Tyr Gln Ser Phe Ala Asp Pro Val Thr Ser
                20                  25                  30

Asn Asp Thr Gly Ile Asn Asp Ser Arg Glu Gly Phe Tyr Ile Ser
                35                  40                  45

Val Lys Tyr Asn Pro Ser Ile Ser His Phe Arg Lys Phe Ser Ala
                50                  55                  60

Glu Glu Ala Pro Ile Asn Gly Asn Thr Ser Ile Thr Lys Lys Val
                65                  70                  75

Phe Gly Leu Lys Lys Asp Gly Asp Ile Ala Gln Ser Ala Asn Phe
                80                  85                  90

Asn Arg Thr Asp Pro Ala Leu Glu Phe Gln Asn Asn Leu Ile Ser
                95                  100                 105

Gly Phe Ser Gly Ser Ile Gly Tyr Ala Met Asp Gly Pro Arg Ile
                110                 115                 120

Glu Leu Glu Ala Ala Tyr Gln Lys Phe Asp Ala Lys Asn Pro Asp
                125                 130                 135

Asn Asn Asp Thr Asn Ser Gly Asp Tyr Tyr Lys Tyr Phe Gly Leu
                140                 145                 150

Ser Arg Glu Asp Ala Ile Ala Asp Lys Lys Tyr Val Val Leu Lys
                155                 160                 165

Asn Glu Gly Ile Thr Phe Met Ser Leu Met Val Asn Thr Cys Tyr
                170                 175                 180

Asp Ile Thr Ala Glu Gly Val Pro Phe Ile Pro Tyr Ala Cys Ala
                185                 190                 195

Gly Val Gly Ala Asp Leu Ile Asn Val Phe Lys Asp Phe Asn Leu
                200                 205                 210

Lys Phe Ser Tyr Gln Gly Lys Ile Gly Ile Ser Tyr Pro Ile Thr
                215                 220                 225

Pro Glu Val Ser Ala Phe Ile Gly Gly Tyr Tyr His Gly Val Ile
                230                 235                 240

Gly Asn Asn Phe Asn Lys Ile Pro Val Ile Thr Pro Val Val Leu
                245                 250                 255

Glu Gly Ala Pro Gln Thr Thr Ser Ala Leu Val Thr Ile Asp Thr
                260                 265                 270

Gly Tyr Phe Gly Gly Glu Val Gly Val Arg Phe Thr Phe
                275                 280

<210> SEQ ID NO 11
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1C

<400> SEQUENCE: 11

Met Asn Cys Lys Lys Phe Phe Ile Thr Thr Ala Leu Ala Leu Pro
                5                   10                  15

Met Ser Phe Leu Pro Gly Ile Leu Leu Ser Glu Pro Val Gln Asp
```

-continued

```
                20                  25                  30

Asp Ser Val Ser Gly Asn Phe Tyr Ile Ser Gly Lys Tyr Met Pro
                35                  40                  45

Ser Ala Ser His Phe Gly Val Phe Ser Ala Lys Glu Glu Lys Asn
                50                  55                  60

Pro Thr Val Ala Leu Tyr Gly Leu Lys Gln Asp Trp Asn Gly Val
                65                  70                  75

Ser Ala Ser Ser His Ala Asp Ala Asp Phe Asn Asn Lys Gly Tyr
                80                  85                  90

Ser Phe Lys Tyr Glu Asn Asn Pro Phe Leu Gly Phe Ala Gly Ala
                95                  100                 105

Ile Gly Tyr Ser Met Gly Gly Pro Arg Ile Glu Phe Glu Val Ser
                110                 115                 120

Tyr Glu Thr Phe Asp Val Lys Asn Gln Gly Gly Asn Tyr Lys Asn
                125                 130                 135

Asp Ala His Arg Tyr Cys Ala Leu Asp Arg Lys Ala Ser Ser Thr
                140                 145                 150

Asn Ala Thr Ala Ser His Tyr Val Leu Leu Lys Asn Glu Gly Leu
                155                 160                 165

Leu Asp Ile Ser Leu Met Leu Asn Ala Cys Tyr Asp Val Val Ser
                170                 175                 180

Glu Gly Ile Pro Phe Ser Pro Tyr Ile Cys Ala Gly Val Gly Thr
                185                 190                 195

Asp Leu Ile Ser Met Phe Glu Ala Ile Asn Pro Lys Ile Ser Tyr
                200                 205                 210

Gln Gly Lys Leu Gly Leu Ser Tyr Ser Ile Asn Pro Glu Ala Ser
                215                 220                 225

Val Phe Val Gly Gly His Phe His Lys Val Ala Gly Asn Glu Phe
                230                 235                 240

Arg Asp Ile Ser Thr Leu Lys Ala Phe Ala Thr Pro Ser Ser Ala
                245                 250                 255

Ala Thr Pro Asp Leu Ala Thr Val Thr Leu Ser Val Cys His Phe
                260                 265                 270

Gly Val Glu Leu Gly Gly Arg Phe Asn Phe
                275                 280

<210> SEQ ID NO 12
<211> LENGTH: 286
<212> TYPE: PRT
<213> ORGANISM: Ehrlichia chaffeensis
<220> FEATURE:
<223> OTHER INFORMATION: amino acid sequence of E. chaffeensis OMP-1D

<400> SEQUENCE: 12

Met Asn Cys Glu Lys Phe Phe Ile Thr Thr Ala Leu Thr Leu Leu
                5                   10                  15

Met Ser Phe Leu Pro Gly Ile Ser Leu Ser Asp Pro Val Gln Asp
                20                  25                  30

Asp Asn Ile Ser Gly Asn Phe Tyr Ile Ser Gly Lys Tyr Met Pro
                35                  40                  45

Ser Ala Ser His Phe Gly Val Phe Ser Ala Lys Glu Glu Arg Asn
                50                  55                  60

Thr Thr Val Gly Val Phe Gly Ile Glu Gln Asp Trp Asp Arg Cys
                65                  70                  75

Val Ile Ser Arg Thr Thr Leu Ser Asp Ile Phe Thr Val Pro Asn
```

-continued

```
                     80                  85                  90
Tyr Ser Phe Lys Tyr Glu Asn Asn Leu Phe Ser Gly Phe Ala Gly
                 95                 100                 105
Ala Ile Gly Tyr Ser Met Asp Gly Pro Arg Ile Glu Leu Glu Val
            110                 115                 120
Ser Tyr Glu Ala Phe Asp Val Lys Asn Gln Gly Asn Asn Tyr Lys
        125                 130                 135
Asn Glu Ala His Arg Tyr Tyr Ala Leu Ser His Leu Leu Gly Thr
    140                 145                 150
Glu Thr Gln Ile Asp Gly Ala Gly Ser Ala Ser Val Phe Leu Ile
                155                 160                 165
Asn Glu Gly Leu Leu Asp Lys Ser Phe Met Leu Asn Ala Cys Tyr
            170                 175                 180
Asp Val Ile Ser Glu Gly Ile Pro Phe Ser Pro Tyr Ile Cys Ala
        185                 190                 195
Gly Ile Gly Ile Asp Leu Val Ser Met Phe Glu Ala Ile Asn Pro
    200                 205                 210
Lys Ile Ser Tyr Gln Gly Lys Leu Gly Leu Ser Tyr Pro Ile Ser
                215                 220                 225
Pro Glu Ala Ser Val Phe Ile Gly Gly His Phe His Lys Val Ile
            230                 235                 240
Gly Asn Glu Phe Arg Asp Ile Pro Thr Met Ile Pro Ser Glu Ser
        245                 250                 255
Ala Leu Ala Gly Lys Gly Asn Tyr Pro Ala Ile Val Thr Leu Asp
    260                 265                 270
Val Phe Tyr Phe Gly Ile Glu Leu Gly Gly Arg Phe Asn Phe Gln
                275                 280                 285
Leu
```

<210> SEQ ID NO 13
<211> LENGTH: 278
<212> TYPE: PRT
<213> ORGANISM: Ehrlichia chaffeensis
<220> FEATURE:
<223> OTHER INFORMATION: amino acid sequence of E. chaffeensis OMP-1E

<400> SEQUENCE: 13

```
Met Asn Cys Lys Lys Phe Phe Ile Thr Thr Ala Leu Val Ser Leu
                  5                  10                  15
Met Ser Phe Leu Pro Gly Ile Ser Phe Ser Asp Pro Val Gln Gly
                 20                  25                  30
Asp Asn Ile Ser Gly Asn Phe Tyr Val Ser Gly Lys Tyr Met Pro
             35                  40                  45
Ser Ala Ser His Phe Gly Met Phe Ser Ala Lys Glu Glu Lys Asn
         50                  55                  60
Pro Thr Val Ala Leu Tyr Gly Leu Lys Gln Asp Trp Glu Gly Ile
     65                  70                  75
Ser Ser Ser Ser His Asn Asp Asn His Phe Asn Asn Lys Gly Tyr
                 80                  85                  90
Ser Phe Lys Tyr Glu Asn Asn Pro Phe Leu Gly Phe Ala Gly Ala
             95                 100                 105
Ile Gly Tyr Ser Met Gly Gly Pro Arg Val Glu Phe Glu Val Ser
        110                 115                 120
Tyr Glu Thr Phe Asp Val Lys Asn Gln Gly Asn Asn Tyr Lys Asn
    125                 130                 135
```

-continued

```
Asp Ala His Arg Tyr Cys Ala Leu Gly Gln Gln Asp Asn Ser Gly
            140                 145                 150

Ile Pro Lys Thr Ser Lys Tyr Val Leu Lys Ser Glu Gly Leu
            155                 160                 165

Leu Asp Ile Ser Phe Met Leu Asn Ala Cys Tyr Asp Ile Ile Asn
            170                 175                 180

Glu Ser Ile Pro Leu Ser Pro Tyr Ile Cys Ala Gly Val Gly Thr
            185                 190                 195

Asp Leu Ile Ser Met Phe Glu Ala Thr Asn Pro Lys Ile Ser Tyr
            200                 205                 210

Gln Gly Lys Leu Gly Leu Ser Tyr Ser Ile Asn Pro Glu Ala Ser
            215                 220                 225

Val Phe Ile Gly Gly His Phe His Lys Val Ile Gly Asn Glu Phe
            230                 235                 240

Arg Asp Ile Pro Thr Leu Lys Ala Phe Val Thr Ser Ser Ala Thr
            245                 250                 255

Pro Asp Leu Ala Ile Val Thr Leu Ser Val Cys His Phe Gly Ile
            260                 265                 270

Glu Leu Gly Gly Arg Phe Asn Phe
            275
```

<210> SEQ ID NO 14
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1F

<400> SEQUENCE: 14

```
Met Asn Cys Lys Lys Phe Phe Ile Thr Thr Thr Leu Val Ser Leu
              5                  10                  15

Met Ser Phe Leu Pro Gly Ile Ser Phe Ser Asp Ala Val Gln Asn
             20                  25                  30

Asp Asn Val Gly Gly Asn Phe Tyr Ile Ser Gly Lys Tyr Val Pro
             35                  40                  45

Ser Val Ser His Phe Gly Val Phe Ser Ala Lys Gln Glu Arg Asn
             50                  55                  60

Thr Thr Thr Gly Val Phe Gly Leu Lys Gln Asp Trp Asp Gly Ser
             65                  70                  75

Thr Ile Ser Lys Asn Ser Pro Glu Asn Thr Phe Asn Val Pro Asn
             80                  85                  90

Tyr Ser Phe Lys Tyr Glu Asn Asn Pro Phe Leu Gly Phe Ala Gly
             95                 100                 105

Ala Val Gly Tyr Leu Met Asn Gly Pro Arg Ile Glu Leu Glu Met
            110                 115                 120

Ser Tyr Glu Thr Phe Asp Val Lys Asn Gln Gly Asn Asn Tyr Lys
            125                 130                 135

Asn Asp Ala His Lys Tyr Tyr Ala Leu Thr His Asn Ser Gly Gly
            140                 145                 150

Lys Leu Ser Asn Ala Gly Asp Lys Phe Val Phe Leu Lys Asn Glu
            155                 160                 165

Gly Leu Leu Asp Ile Ser Leu Met Leu Asn Ala Cys Tyr Asp Val
            170                 175                 180

Ile Ser Glu Gly Ile Pro Phe Ser Pro Tyr Ile Cys Ala Gly Val
            185                 190                 195
```

```
Gly Thr Asp Leu Ile Ser Met Phe Glu Ala Ile Asn Pro Lys Ile
            200                 205                 210

Ser Tyr Gln Gly Lys Leu Gly Leu Ser Tyr Ser Ile Ser Pro Glu
            215                 220                 225

Ala Ser Val Phe Val Gly Gly His Phe His Lys Val Ile Gly Asn
            230                 235                 240

Glu Phe Arg Asp Ile Pro Ala Met Ile Pro Ser Thr Ser Thr Leu
            245                 250                 255

Thr Gly Asn His Phe Thr Ile Val Thr Leu Ser Val Cys His Phe
            260                 265                 270

Gly Val Glu Leu Gly Gly Arg Phe Asn Phe
            275                 280

<210> SEQ ID NO 15
<211> LENGTH: 284
<212> TYPE: PRT
<213> ORGANISM: Cowdria ruminantium
<220> FEATURE:
<223> OTHER INFORMATION: amino acid sequence of C. ruminantium MAP-1

<400> SEQUENCE: 15

Met Asn Cys Lys Lys Ile Phe Ile Thr Ser Thr Leu Ile Ser Leu
              5                  10                  15

Val Ser Phe Leu Pro Gly Val Ser Phe Ser Asp Val Ile Gln Glu
             20                  25                  30

Glu Asn Asn Pro Val Gly Ser Val Tyr Ile Ser Ala Lys Tyr Met
             35                  40                  45

Pro Thr Ala Ser His Phe Gly Lys Met Ser Ile Lys Glu Asp Ser
             50                  55                  60

Arg Asp Thr Lys Ala Val Phe Gly Leu Lys Lys Asp Trp Asp Gly
             65                  70                  75

Val Lys Thr Pro Ser Gly Asn Thr Asn Ser Ile Phe Thr Glu Lys
             80                  85                  90

Asp Tyr Ser Phe Lys Tyr Glu Asn Asn Pro Phe Leu Gly Phe Ala
             95                 100                 105

Gly Ala Val Gly Tyr Ser Met Asn Gly Pro Arg Ile Glu Phe Glu
            110                 115                 120

Val Ser Tyr Glu Thr Phe Asp Val Arg Asn Pro Gly Gly Asn Tyr
            125                 130                 135

Lys Asn Asp Ala His Met Tyr Cys Ala Leu Asp Thr Ala Ser Ser
            140                 145                 150

Ser Thr Ala Gly Ala Thr Thr Ser Val Met Val Lys Asn Glu Asn
            155                 160                 165

Leu Thr Asp Ile Ser Leu Met Leu Asn Ala Cys Tyr Asp Ile Met
            170                 175                 180

Leu Asp Gly Met Pro Val Ser Pro Tyr Val Cys Ala Gly Ile Gly
            185                 190                 195

Thr Asp Leu Val Ser Val Ile Asn Ala Thr Asn Pro Lys Leu Ser
            200                 205                 210

Tyr Gln Gly Lys Leu Gly Ile Ser Tyr Ser Ile Asn Pro Glu Ala
            215                 220                 225

Ser Ile Phe Ile Gly Gly His Phe His Arg Val Ile Gly Asn Glu
            230                 235                 240

Phe Lys Asp Ile Ala Thr Ser Lys Val Phe Thr Ser Ser Gly Asn
            245                 250                 255
```

Ala Ser Ser Ala Val Ser Pro Gly Phe Ala Ser Ala Ile Leu Asp
            260                 265                 270

Val Cys His Phe Gly Ile Glu Ile Gly Gly Arg Phe Val Phe
            275                 280

<210> SEQ ID NO 16
<211> LENGTH: 20
<212> TYPE: DNA
<213> ORGANISM: artificial sequence
<220> FEATURE:
<221> NAME/KEY: primer_bind
<222> LOCATION: nucleotides 313-332 of C. ruminantium MAP-1,
<223> OTHER INFORMATION: forward primer 793 for PCR

<400> SEQUENCE: 16
gcaggagctg ttggttactc                                              20

<210> SEQ ID NO 17
<211> LENGTH: 21
<212> TYPE: DNA
<213> ORGANISM: artificial sequence
<220> FEATURE:
<221> NAME/KEY: primer_bind
<222> LOCATION: nucleotides 823-843 of C. ruminantium MAP-1,
<223> OTHER INFORMATION: reverse primer 1330 for PCR

<400> SEQUENCE: 17
ccttcctcca agttctatgc c                                            21

<210> SEQ ID NO 18
<211> LENGTH: 24
<212> TYPE: DNA
<213> ORGANISM: artificial sequence
<220> FEATURE:
<221> NAME/KEY: primer_bind
<223> OTHER INFORMATION: primer 46f, specific for ECa28SA2 gene

<400> SEQUENCE: 18
atatacttcc tacctaatgt ctca                                         24

<210> SEQ ID NO 19
<211> LENGTH: 20
<212> TYPE: DNA
<213> ORGANISM: artificial sequence
<220> FEATURE:
<221> NAME/KEY: primer_bind
<223> OTHER INFORMATION: primer used for sequencing 28-kDa protein genes
      in E. canis

<400> SEQUENCE: 19
agtgcagagt cttcggtttc                                              20

<210> SEQ ID NO 20
<211> LENGTH: 18
<212> TYPE: DNA
<213> ORGANISM: artificial sequence
<220> FEATURE:
<221> NAME/KEY: primer_bind
<223> OTHER INFORMATION: primer used for sequencing 28-kDa protein genes
      in E. canis

<400> SEQUENCE: 20
gttacttgcg gaggacat                                                18

<210> SEQ ID NO 21
<211> LENGTH: 24

```
<212> TYPE: DNA
<213> ORGANISM: artificial sequence
<220> FEATURE:
<221> NAME/KEY: primer_band
<222> LOCATION: nucleotides 687-710 of ECa28-1
<223> OTHER INFORMATION: primer 394 for PCR

<400> SEQUENCE: 21
gcatttccac aggatcatag gtaa                                              24

<210> SEQ ID NO 22
<211> LENGTH: 24
<212> TYPE: DNA
<213> ORGANISM: artificial sequence
<220> FEATURE:
<221> NAME/KEY: primer_band
<222> LOCATION: nucleotides 710-687 of ECa28-1
<223> OTHER INFORMATION: primer 394C for PCR

<400> SEQUENCE: 22
ttacctatga tcctgtggaa atgc                                              24

<210> SEQ ID NO 23
<211> LENGTH: 20
<212> TYPE: DNA
<213> ORGANISM: artificial sequence
<220> FEATURE:
<221> NAME/KEY: primer_bind
<223> OTHER INFORMATION: primer 793C which anneals to a region with
      Eca28-1, used to amplify the intergenic region between gene
      ECa28SA3 and ECa28-1

<400> SEQUENCE: 23
gagtaaccaa cagctcctgc                                                   20

<210> SEQ ID NO 24
<211> LENGTH: 24
<212> TYPE: DNA
<213> ORGANISM: artificial sequence
<220> FEATURE:
<221> NAME/KEY: primer_band
<222> LOCATION:
<223> OTHER INFORMATION: primer EC28OM-F complementary to noncoding
      regions adjacent to the open reading frame of ECa28-1

<400> SEQUENCE: 24
tctactttgc acttccacta ttgt                                              24

<210> SEQ ID NO 25
<211> LENGTH: 24
<212> TYPE: DNA
<213> ORGANISM: artificial sequence
<220> FEATURE:
<221> NAME/KEY: primer_band
<222> LOCATION:
<223> OTHER INFORMATION: primer EC28OM-R complementary to noncoding
      regions adjacent to the open reading frame of ECa28-1

<400> SEQUENCE: 25
attcttttgc cactattttt cttt                                              24

<210> SEQ ID NO 26
<211> LENGTH: 25
<212> TYPE: DNA
<213> ORGANISM: artificial sequence
<220> FEATURE:
<221> NAME/KEY: primer_bind
<223> OTHER INFORMATION: primer ECaSA3-2 corresponding to regions within
      ECa28SA3, used to amplify the intergenic region NC3
``` between gene ECa28SA3 and ECa28-1

<400> SEQUENCE: 26
ctaggattag gttatagtat aagtt                                         25

<210> SEQ ID NO 27
<211> LENGTH: 23
<212> TYPE: PRT
<213> ORGANISM: Ehrlichia canis
<220> FEATURE:
<221> NAME/KEY: PEPTIDE
<223> OTHER INFORMATION: a predicted N-terminal signal peptide of
      ECa28-1 and ECa28SA3

<400> SEQUENCE: 27

Met Asn Cys Lys Lys Ile Leu Ile Thr Thr Ala Leu Met Ser Leu
                 5                  10                  15

Met Tyr Tyr Ala Pro Ser Ile Ser
             20

<210> SEQ ID NO 28
<211> LENGTH: 25
<212> TYPE: PRT
<213> ORGANISM: Ehrlichia chaffeensis
<220> FEATURE:
<223> OTHER INFORMATION: amino acid sequence of N-terminal signal
      peptide of E. chaffeensis P28

<400> SEQUENCE: 28

Met Asn Tyr Lys Lys Ile Leu Ile Thr Ser Ala Leu Ile Ser Leu
                 5                  10                  15

Ile Ser Ser Leu Pro Gly Val Ser Phe Ser
             20                  25

<210> SEQ ID NO 29
<211> LENGTH: 26
<212> TYPE: PRT
<213> ORGANISM: Ehrlichia canis
<220> FEATURE:
<223> OTHER INFORMATION: amino acid sequence of putative cleavage site
      of ECa28-1

<400> SEQUENCE: 29

Met Asn Cys Lys Lys Ile Leu Ile Thr Thr Ala Leu Ile Ser Leu
                 5                  10                  15

Met Tyr Ser Ile Pro Ser Ile Ser Ser Phe Ser
             20                  25

<210> SEQ ID NO 30
<211> LENGTH: 299
<212> TYPE: DNA
<213> ORGANISM: Ehrlichia canis
<220> FEATURE:
<223> OTHER INFORMATION: nucleic acid sequence of intergenic noncoding
      region 1 (28NC1)

<400> SEQUENCE: 30
taatacttct attgtacatg ttaaaaatag tactagtttg cttctgtggt ttataaacgc      60
aagagagaaa tagttagtaa taaattagaa agttaaatat tagaaaagtc atatgttttt    120
cattgtcatt gatactcaac taaaagtagt ataaatgtta cttattaata attttacgta    180
gtatattaaa tttcccttac aaaagccact agtatttat actaaaagct atactttggc    240
ttgtatttaa tttgtatttt tactactgtt aatttacttt cactgtttct ggtgtaaat    299

<210> SEQ ID NO 31
<211> LENGTH: 345
<212> TYPE: DNA
<213> ORGANISM: Ehrlichia canis
<220> FEATURE:
<223> OTHER INFORMATION: nucleic acid sequence of intergenic noncoding region 2 (28NC2)

<400> SEQUENCE: 31

```
taatttcgtg gtacacatat cacgaagcta aaattgtttt tttatctctg ctgtatacaa      60
gagaaaaaat agtagtgaaa attacctaac aatatgacag tacaagttta ccaagcttat     120
tctcacaaaa cttcttgtgt cttttatctc tttacaatga aatgtacact tagcttcact     180
actgtagagt gtgtttatca atgctttgtt tattaatact ctacataata tgttaaattt     240
ttcttacaaa actcactagt aatttatact agaatatata ttctgacttg tatttgcttt     300
atacttccac tattgttaat ttattttcac tattttaggt gtaat                     345
```

<210> SEQ ID NO 32
<211> LENGTH: 345
<212> TYPE: DNA
<213> ORGANISM: Ehrlichia canis
<220> FEATURE:
<223> OTHER INFORMATION: nucleic acid sequence of intergenic noncoding region 3 (28NC3)

<400> SEQUENCE: 32

```
tgattttatt gttgccacat attaaaaatg atctaaactt gtttttatta ttgctacata      60
caaaaaaaag aaaatagtg gcaaaagaat gtagcaataa gagggggggg ggggactaaa     120
tttaccttct attcttctaa tattctttac tatattcaaa tagcacaact caatgcttcc     180
aggaaaatat gtttctaata ttttatttat taccaatcct tatataatat attaaatttc     240
tcttacaaaa atctctaatg ttttatactt aaatatatata ttctggcttg tatttactttt    300
gcacttccac tattgttaat ttattttcac tattttaggt gtaat                     345
```

<210> SEQ ID NO 33
<211> LENGTH: 355
<212> TYPE: DNA
<213> ORGANISM: Ehrlichia canis
<220> FEATURE:
<223> OTHER INFORMATION: nucleic acid sequence of intergenic noncoding region 4 (28NC4)

<400> SEQUENCE: 33

```
taattttatt gttgccacat attaaaaatg atctaaactt gtttttawta ttgctacata      60
caaaaaaaga aaatagtgg caaaagaatg tagcaataag agggggggg gggaccaaat      120
ttatcttcta tgcttcccaa gttttttcyc gctatttatg acttaaacaa cagaaggtaa    180
tatcctcacg gaaaacttat cttcaaatat tttatttatt accaatctta tataatatat    240
taaatttctc ttacaaaaat cactagtatt ttataccaaa atatatattc tgacttgctt    300
ttcttctgca cttctactat ttttaattta tttgtcacta ttaggttata ataaw          355
```